US010209176B2

(12) United States Patent
Proskurowski et al.

(10) Patent No.: US 10,209,176 B2
(45) Date of Patent: Feb. 19, 2019

(54) FLUID FLOW CELL INCLUDING A SPHERICAL LENS

(71) Applicant: MarqMetrix Inc., Seattle, WA (US)

(72) Inventors: Giora Proskurowski, Seattle, WA (US); Brian James Marquardt, Seattle, WA (US)

(73) Assignee: MarqMetrix, Inc., Seattle, WA (US)

( * ) Notice: Subject to any disclaimer, the term of this patent is extended or adjusted under 35 U.S.C. 154(b) by 0 days.

(21) Appl. No.: 15/908,628

(22) Filed: Feb. 28, 2018

(65) Prior Publication Data

US 2018/0246031 A1 Aug. 30, 2018

Related U.S. Application Data

(60) Provisional application No. 62/606,133, filed on May 4, 2017, provisional application No. 62/464,994, filed on Feb. 28, 2017.

(51) Int. Cl.
*G01N 21/01* (2006.01)
*G01N 21/03* (2006.01)
*G01N 21/05* (2006.01)
*G01N 21/65* (2006.01)

(52) U.S. Cl.
CPC ......... *G01N 21/01* (2013.01); *G01N 21/0303* (2013.01); *G01N 21/05* (2013.01); *G01N 21/65* (2013.01); *G01N 2021/0106* (2013.01); *G01N 2021/651* (2013.01); *G01N 2201/068* (2013.01)

(58) Field of Classification Search
CPC .... G01N 21/05; G01N 21/0303; G01N 21/01; G01N 21/65

USPC .......................................................... 356/437
See application file for complete search history.

(56) References Cited

U.S. PATENT DOCUMENTS

| | | | |
|---|---|---|---|
| 4,459,859 A | 7/1984 | Price et al. | |
| 4,676,639 A | 6/1987 | Van Wagenen | |
| 9,835,545 B2 * | 12/2017 | Furuya | G01N 21/05 |
| 2001/0010747 A1 | 8/2001 | Dourdeville et al. | |
| 2004/0008345 A1 | 1/2004 | Nurmikko et al. | |
| 2004/0165183 A1 | 8/2004 | Marquardt et al. | |
| 2004/0256560 A1 | 12/2004 | Russell | |
| 2009/0216463 A1 | 8/2009 | Xie et al. | |
| 2016/0161705 A1 | 6/2016 | Marquardt et al. | |
| 2016/0238517 A1 * | 8/2016 | Furuya | G01N 21/05 |

OTHER PUBLICATIONS

PCT Search Report and Written Opinion dated May 16, 2018 for PCT Application No. PCT/US18/20312, 8 pages.

\* cited by examiner

*Primary Examiner* — Roy M Punnoose
(74) *Attorney, Agent, or Firm* — Lee & Hayes, P.C.

(57) ABSTRACT

A flow cell device including a spherical optical element is disclosed. The spherical lens can be sealed to the body of the flow cell device in a manner that provides external optical access to a fluid in an analysis region of a flow path through the flow cell device. The seal can be provided by an elastomer, a polymer, or a deformable metal. The disposition of the spherical lens to the flow path enables in situ optical analysis of the fluid. An optical analysis device can be removably connected to the flow cell device to provide the optical analysis. In some embodiments the optical analysis device is a portable Raman spectrometer. The flow cell device can provide a supplementary interrogation interface, and/or an on board sensor device(s) to enable multivariate analysis and/or advanced triggering.

22 Claims, 17 Drawing Sheets

FLUID FLOW CELL INCLUDING A SPHERICAL LENS

CROSS REFERENCE TO RELATED APPLICATIONS

This application claims priority to commonly assigned, U.S. Provisional Patent Application Ser. No. 62/606,133, filed May 4, 2017, and to commonly assigned, U.S. Provisional Patent Application Ser. No. 62/464,994, filed Feb. 28, 2017. Application Ser. No. 62/606,133 and Application Ser. No. 62/464,994 are each fully incorporated herein by reference.

TECHNICAL FIELD

The disclosed subject matter relates to a flow cell facilitating optical interrogation of a fluid flowing through the flow cell, and, for example, to a flow cell including a spherical lens element disposed to enable optical interrogation of a fluid flowing through the flow cell.

BACKGROUND

Conventional optical spectroscopy of flowing fluids is generally performed via an optical probe device that is inserted through a port into a fluid flow region. These optical probe devices can include a 'window' optical element, e.g., a non-refractive optical element that typically can be disposed between the refractive optical elements of the optical probe device and the sample flow, e.g., the optical probe device can have a tip that is inserted through a port into the flow, wherein the tip can include a window element to protect the refractive optical elements within the optical probe device.

SUMMARY

In an aspect, the disclosed subject matter provides for a flow cell device (FCD) that enables removably connecting an optical analysis device, e.g., a portable Raman spectrometer, to an attachment point of the flow cell device allowing for interrogation of fluids in an analysis zone ("analysis zone" used interchangeably with "analysis region" herein). The removable connection is intended to provide for ready disconnection of the optical analysis device to allow other points in the fluidic system equipped with similar FCDs to be interrogated by removably attaching the optical analysis devices at those other FCDs. It will be appreciated that an optical analysis device can be left attached to the attachment point where removal of the optical analysis device is not desired or needed. However, the practical advantages of a technician carrying an optical analysis device to different test points in a process line and readily attaching the optical analysis device to a FCD at each test point to gather data for that point will be appreciated to typically be superior to the complexities of plumbing sample transport lines to a dedicated single flow cell, and/or the expense of multiple optical analysis instruments fixed at each test point, etc.

In another aspect, the FCD can include a spherical optical element (SOE), e.g., a spherical lens, ball lens, etc. The SOE can be disposed so as to be part of the fluid path, e.g., as part of the fluid path wall. In an aspect, the SOE can be sealed into an orifice defined in the fluid path wall such that flowing a fluid through the fluid path results in the fluid flowing directly past and in contact with the SOE. The SOE can be sealed in place to prevent fluid leaking past the SOE, e.g., via an elastomer, a polymer, a deformable metal seal, an epoxy, or other sealants, etc. Optical energy can then be passed into an analysis zone defined by the optics of the optical analysis device and the SOE. This can enable seamless integration of the measurement interface into the fluid flow path.

DETAILED DESCRIPTION

Figure 1:
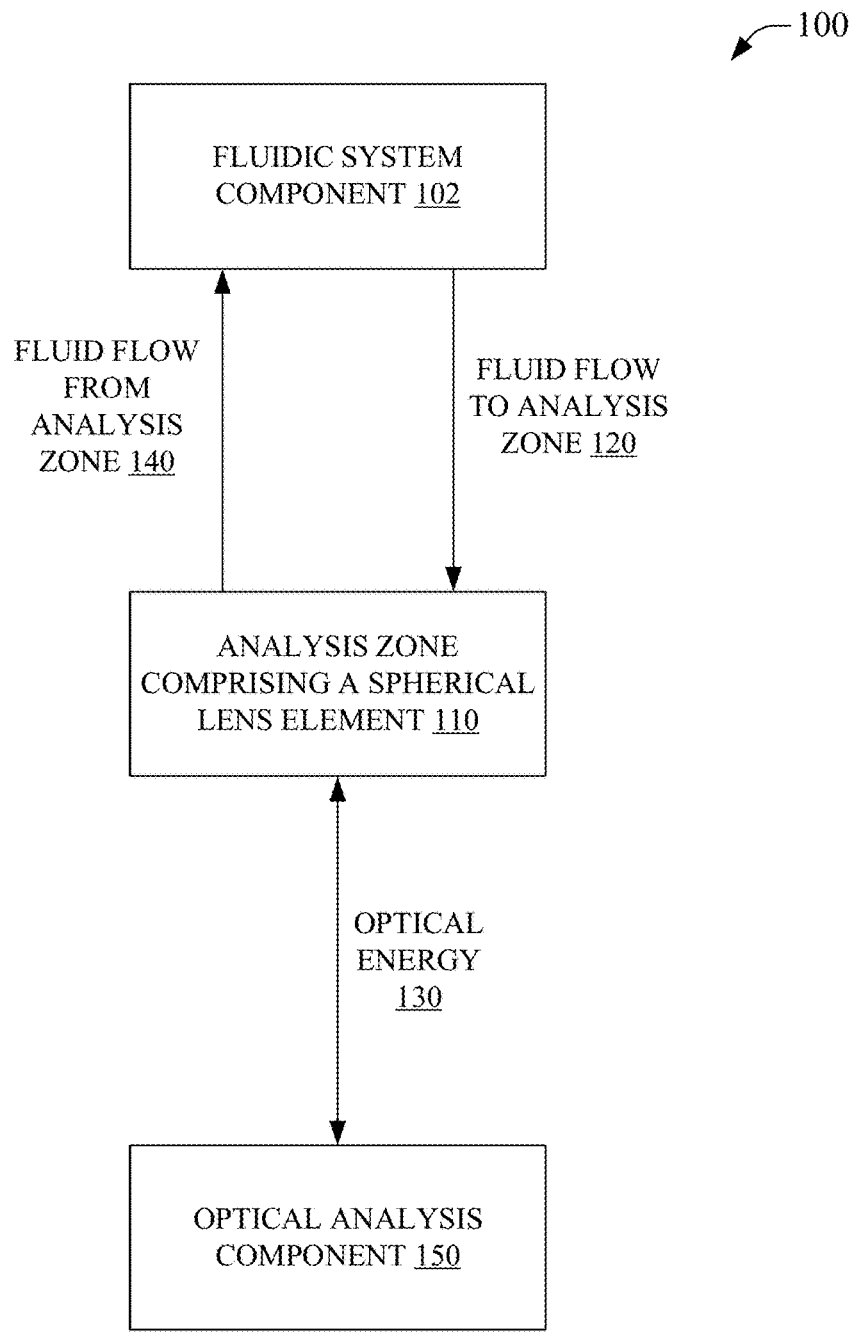
FIG. 1 is an illustration of an example system that can facilitate optical interrogation of a sample flowing into an analysis zone defined, at least in part, by a spherical optical element that can conduct optical energy between a flow cell device including the spherical optical element and an optical analysis instrument, in accordance with aspects of the subject disclosure.

The subject disclosure is now described with reference to the drawings, wherein like reference numerals are used to refer to like elements throughout. In the following description, for purposes of explanation, numerous specific details are set forth in order to provide a thorough understanding of the subject disclosure. It may be evident, however, that the subject disclosure may be practiced without these specific details. In other instances, well-known structures and devices are shown in block diagram form in order to facilitate describing the subject disclosure.

Typically, conventional optical analysis of a flowing fluid can either be performed in-situ by inserting an optical probe device into a flowing sample via an insertion port plumbed into the fluidic system of interest, or can transport a sample of the fluid to a flow cell of an optical analysis instrument, e.g., wherein the optical analysis instrument is generally fixedly disposed relative to the flow cell. Both of these conventional approaches can have drawbacks, e.g., contamination via an insertion port, complex plumbing where samples from different points of a fluidic process are transported to a single optical analysis flow cell, cross contamination in running multiple streams through a same flow cell, altering fluidic conditions, e.g., temperature, flow rate, etc., by tapping off a fluid for transport to an external flow cell, etc. It can be desirable to perform optical analysis of fluids in situ without use of an inserted probe. Moreover, where an optical analysis device can be readily connected and disconnected from an optical sampling at the fluidic device, an added benefit of moving the optical analysis device between different analysis location in the fluidic system can reduce the complexities of plumbing and contamination associated with using a single flow cell, or with a single conventional probe, for analysis of multiple points in a fluid system.

In an aspect, the disclosed subject matter provides for a flow cell device (FCD) that enables removably connecting an optical analysis device, e.g., a portable Raman spectrometer, to an attachment point of the flow cell device allowing for interrogation of fluids in an analysis zone ("analysis zone" is used interchangeably with "analysis region" herein). The removable connection is intended to provide for ready disconnection of the optical analysis device to allow other points in the fluidic system equipped with similar FCDs to be interrogated by removably attaching the optical analysis devices at those other FCDs. It will be appreciated that an optical analysis device can be left attached to the attachment point where removal of the optical analysis device is not desired or needed. However, the practical advantages of a technician carrying an optical analysis device to different test points in a process line and readily attaching the optical analysis device to a FCD at each test point to gather data for that point will be appreciated to typically be superior to the complexities of plumbing sample transport lines to a dedicated single flow cell, and/or the expense of multiple optical analysis instruments fixed at each test point, etc.

In another aspect, the FCD can include a spherical optical element (SOE), e.g., a spherical lens, ball lens, etc. The SOE can be disposed so as to be part of the fluid path, e.g., as part of the fluid path wall. In an aspect, the SOE can be sealed into an orifice defined in the fluid path wall such that flowing a fluid through the fluid path results in the fluid flowing directly past and in contact with the SOE. The SOE can be sealed in place to prevent fluid leaking past the SOE, e.g., via an elastomer, a deformable metal seal, etc. Optical energy can then be passed into an analysis zone defined by the optics of the optical analysis device and the SOE. "Spherical optical element," or similar terms, can refer to an optical element, e.g., a lens, etc., that has a spherical, or nearly spherical, geometry. Moreover, the term "spherical optical element," as used herein, can also include any optical element that conducts light via a portion of an optical element that includes a curved surface approximating at least a portion of a sphere. As an example, an optical element including two individual generally hemispherical portions can also be considered a spherical element within the scope of the instant disclosure. As particular examples, optics similar to, or the same as, those disclosed in U.S. Pat. No. 6,831,745, entitled "Optical Immersion Probe Incorporating a Spherical Lens," and U.S. Pat. No. 6,977,729, also entitled "Optical Immersion Probe Incorporating a Spherical Lens," the entireties of which applications are hereby incorporated by reference herein, can be employed to perform, for example, Raman spectroscopy of a fluid in the analysis zone.

To the accomplishment of the foregoing and related ends, the disclosed subject matter, then, includes one or more of the features hereinafter more fully described. The following description and the annexed drawings set forth in detail certain illustrative aspects of the subject matter. However, these aspects are indicative of but a few of the various ways in which the principles of the subject matter can be employed. Other aspects, advantages, and novel features of the disclosed subject matter will become apparent from the following detailed description when considered in conjunction with the provided drawings.

FIG. 1 is an illustration of a system 100, which can facilitate optical interrogation of a sample flowing into an analysis zone defined, at least in part, by a spherical optical element that can conduct optical energy between a flow cell device including the spherical optical element and an optical analysis instrument, in accordance with aspects of the subject disclosure. System 100 can include fluidic system component 102. Fluidic system component 102 can be part of a fluidic system, e.g., a microfluidic system, a process line having fluidic stages, etc. Fluid can flow from fluidic system component 102 to and from analysis zone including a spherical lens element 110, e.g., via fluid flow to analysis zone 120 and fluid flow from analysis zone 140. The fluid can be any suitable type of fluid or material, including, without limitation, a liquid, gas, slurry, suspension, heterogeneous mixture of liquid and solid, powder, aerosol or other flowing solid material (e.g., peanut butter), or any other fluid. In an aspect, fluidic system component 102 can be a line or pipe transporting fluid in a fluidic system, wherein fluidic system component 102, e.g., the line or pipe can have inserted therein a device defining an analysis zone, e.g., analysis zone including a spherical lens element 110, such as an analysis zone defined in a flow cell device (FCD) as disclosed herein. For simplicity, in the context of the disclosed subject matter, the terms analysis zone including a spherical lens element, e.g., 110, can be simply referred to as an 'analysis zone,' wherein all analysis zones disclosed herein are, except where explicitly stated otherwise, to include or be defined, at least in part, by a spherical lens element.

System 100 can further include optical analysis component 150 that can facilitate performing an optical analysis of a fluid in analysis zone 110. Optical energy 130 can be communicated between optical analysis component 150 and analysis zone 110 via the spherical lens element that analysis zone 110 includes. In an aspect, optical analysis component 150 can be an optical emitter and/or receiver portion of nearly any optical analytical device. For the sake of clarity and brevity, optical analysis component 150 will generally be discussed in terms of a portable Raman spectrometer device, although the disclosed subject matter is expressly not so limited and is intended to include nearly any other optical analysis, e.g., infrared (IR) spectroscopy, Raman spectroscopy, ultraviolet-visual (UV-Vis) spectroscopy, near infrared (NIR)spectroscopy, reflectance spectroscopy, absorption spectroscopy, scattering spectroscopy, fluorescence spectroscopy, or any other optical technique, particularly those utilizing a co-located light source and detector, among others.

In some embodiments, analysis zone 110 can be included in a FCD inserted into a fluid transport line, for example in an oil refinery, pharmaceutical plant, municipal water treatment facility, etc., such that a fluid of interest passes through an analysis zone defined in part by a SOE, e.g., a spherical lens. The SOE can enable passing optical energy 130, such as a laser, etc., from optical analysis component 150, e.g., a portable Raman spectrometer, etc., into the analysis zone via the SOE to interrogate a fluid flowing past the SOE, e.g., the fluid flowing in via fluid flow to analysis zone. The laser, e.g., optical energy 130, can interact with the sample in the analysis zone and Raman shifted light, e.g., optical energy 130, can be collected via the SOE and returned to optical analysis component 150 for analysis and interpretation. In this example embodiment, the portable Raman spectrometer can be carried to different FCDs deployed in the oil refinery, pharmaceutical plant, municipal water treatment facility, etc., to allow collection of Raman spectra for different fluidic test points. This embodiment illustrates that the inclusion of the SOE into the analysis zone 110 provides direct interrogation of the fluid in the analysis zone via the SOE by simply passing in optical energy and collecting resulting optical energy. As such, connection of an optical analysis component 150 can be simple and easy to connect and disconnect without disturbing the fluidic system. Moreover, by not directly inserting an optical probe, via a probe port, into the fluid, the possibility of contamination is reduced, the need to clean/sanitize, the optical probe is reduced, etc.

In a particular example embodiment, such as a Marqmetrix® Process Elite Flow Cell BallProbe®, the analysis zone 110 can be included in a FCD formed from, for example, Hastelloy™, etc., and having dimensions of approximately 3.5 cm in length, 2 cm in height, and 1.3 cm in depth. This particular example can further include a SOE of approximately 6 mm in diameter. In some versions of this example embodiment, the SOE can be sapphire, for example, UV-grade sapphire, etc. The SOE can be sealed against fluid incursion by, for example, perflouroelastomer, such as Kalrez™, etc., or a deformable metal, e.g., gold, an epoxy, or other sealants, etc., where predicted environmental conditions in the fluid path dictate. In this particular example, the clear aperture of an interrogating laser, e.g., a maximum laser beam waist, can be approximately 5.6 mm. The example embodiment can be plumbed into a fluidic line with standard connections, e.g., ⅛" Swagelok™, Parker™ A-lok-™fittings, ¼-28 flangeless fittings, low-, medium- and high-pressure fittings, coned fittings, threaded fittings, nominal pipe thread (NPT) fittings, face-sealing fittings, piston-sealing fittings, other standard plumbing connector fittings, etc.

Figure 2:
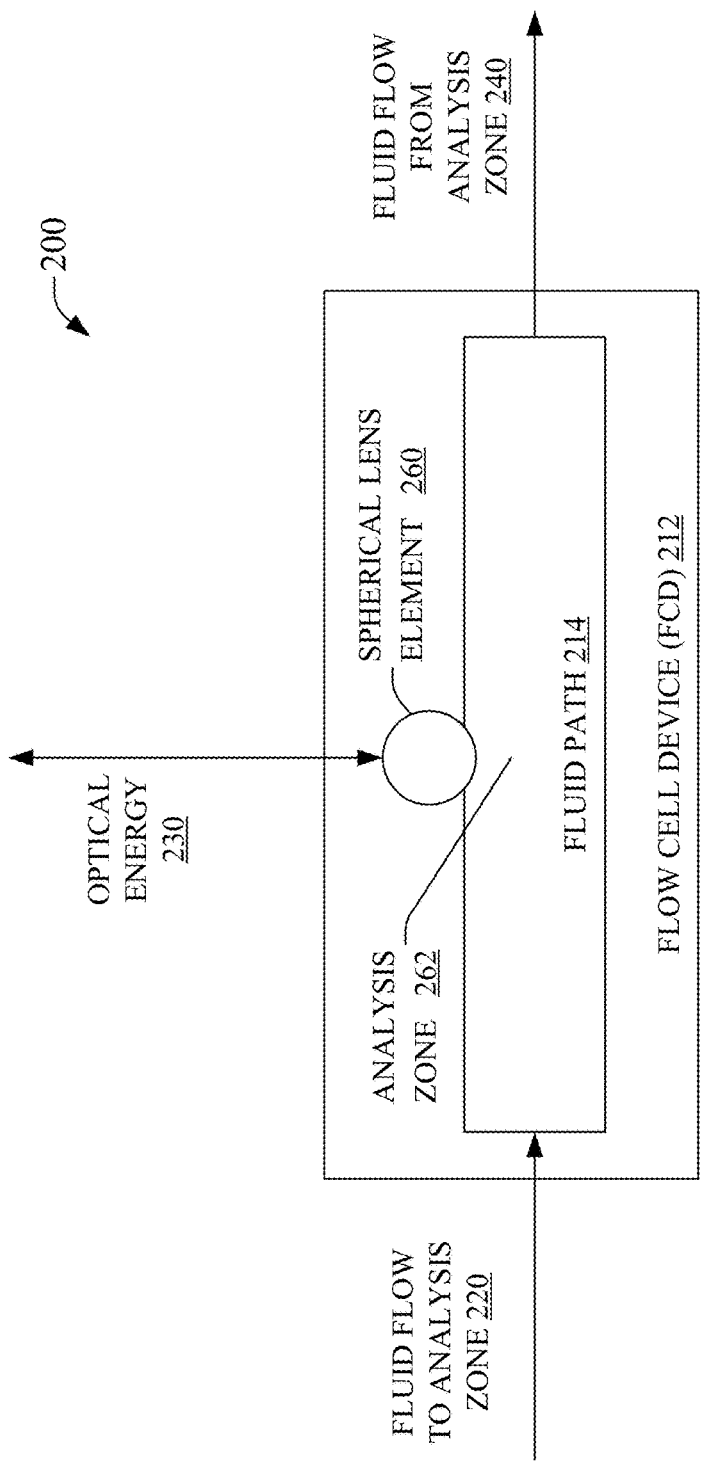
FIG. 2 is an illustration of an example system that can enable transmitting optical energy in and out of an analysis zone via a spherical optical element of flow cell device, in accordance with aspects of the subject disclosure.

FIG. 2 is an illustration of a system 200, which can facilitate transmitting optical energy in and out of an analysis zone via a spherical optical element of flow cell device, in accordance with aspects of the subject disclosure. System 200 can include flow cell device (FCD) 212. FCD 212 can provide fluid path 214 to facilitate the transport of a fluid through analysis zone 262. Analysis zone 262 can be proximate to a SOE, e.g., spherical lens element 260. Spherical lens element 260 can define a portion of a boundary of fluid path 214, e.g., spherical lens element 260 can act as part of the wall of a tunnel through FCD 212 that carries a flowing fluid. Fluid flow can be introduced to fluid path 214 as fluid flow to analysis zone 220. Fluid can flow from fluid flow to analysis zone 220 to fluid flow from analysis zone 240 via fluid path 214 and, as such, can transition through analysis zone 262.

In an aspect, spherical lens element 260 can enable optical energy 230 to be passed into and out of analysis zone 262 from outside of the fluid path. Whereas fluid flow to analysis zone 220 can be introduced through a sealed connection between fluid path 214 of FCD 212 and a fluidic system component, e.g., 102, etc., and whereas fluid flow from analysis zone 240 can similarly be facilitated by sealed connection between fluid path 214 of FCD 212 and a fluidic system component, e.g., 102, etc., spherical lens element 260 can provide for optical interrogation of an in situ sample, e.g., the fluid at analysis zone 262, by an external optical analysis device, e.g., via optical analysis component 150, etc. This can enable seamless integration of the measurement interface into the fluid flow path. In an aspect, spherical lens element 260 can be provided in a conduit to which removable optical analysis components, e.g., 150, etc., can be attached and detached from FCD 212. In some embodiments, the spherical lens element 260 can be complemented by additional fluid interrogation features, e.g., 370, etc., to create a multivariate measurement location of the fluid at analysis zone 262 of fluid path 214.

In some embodiments, FCD 212 can include one or more materials, e.g., a metal, plastic, glass, etc. Some embodiments of FCD 212 can include fluid path 214 as a tunnel through the material forming FCD 212. In other embodiments of FCD 212 fluid path 214 can be at least partly defined by a component of a different material than the material forming FCD 212 and the material forming the component defining the fluid path 214 can be supported by the material forming FCD 212, e.g., fluid path 214 can be defined in a component such as a stainless steel tube that is supported in, for example, a thermoplastic body forming FCD 212. Spherical lens element 260 can be formed of an optical material that has properties germane to the operational environment of the fluids expected to be encountered. Spherical lens element 260 can be formed of the same or different materials as the component defining the fluid path 214 and/or FCD 212. Thus, in some embodiments, the spherical lens element 260 may define a portion of the boundary of the fluid path 214 and may be made of a first material, while a component, such as a tube supported in a body of the FCD 212, may define a remaining portion of the boundary of the fluid path 214 and may be made of a second material different from the first material, and the FCD 212 supporting the component (e.g., tube made of the second material) may be made of a third material different from the first material and/or the second material. As an example, spherical lens element 260 can be sapphire that is sealed into an opening in fluid path 214, which can be formed by an opening through, for example, a Hastelloy™ body of FCD 212. Spherical lens element 260 can be sealed against the opening in fluid path 214 via a material that can be the same or different from other materials of fluid path 214, FCD 212, and/or spherical lens element 260, for example, the seal can be via an elastomer, e.g., buna-N, etc., a polymer, e.g., Delrin™, etc., a deformable metal, e.g., gold, an epoxy, or other sealants, etc. The selection of the sealing material can be based on the expected operating environment. In an aspect, the connections providing for fluid flow to/from the analysis zone, e.g., 220, 240, etc., can be based on any type of connector, and can include low-, medium- and high-pressure fittings including ferrule compression, conical, and coned-and-threaded mechanisms, a welded device, a brazed device, or a soldered device. Optical energy 230 can be conducted via an interface, e.g., optical analysis device connector 416, etc., that can serve as a connection to a removable optical analysis device, and can be of various lengths and/or diameter. In some embodiments an optical analysis device can be hard mounted to the interface. The optical energy connection can include heating/cooling features such as fins, liquid circulators, thermoelectric devices, etc., to adapt or maintain the temperature of the optical interface in view of heating/cooling effects associated with the fluid flow, e.g., where the fluid is super-cooled, the optical interface can be heated to compensate for heat loss to the fluid.

Figure 3:
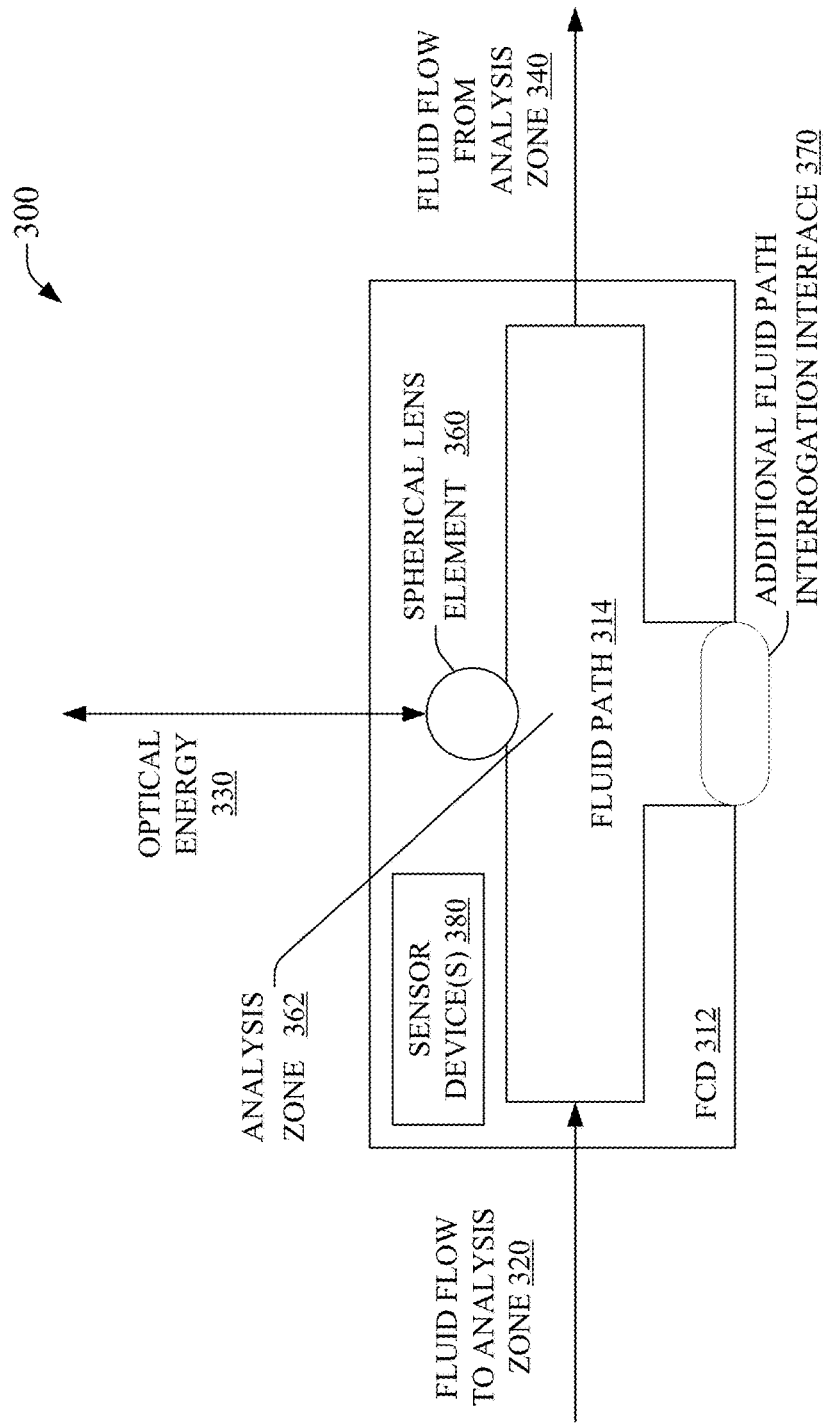
FIG. 3 is an illustration of an example system that can facilitate transmitting optical energy in and out of an analysis zone via a spherical optical element of flow cell device and provides a supplemental interrogation interface for fluids in flowing through a fluid path, in accordance with aspects of the subject disclosure.

FIG. 3 is an illustration of a system 300, which can facilitate transmitting optical energy in and out of an analysis zone via a spherical optical element of flow cell device and provides a supplemental interrogation interface for fluids in flowing through a fluid path, in accordance with aspects of the subject disclosure. System 300 can include flow cell device (FCD) 312. FCD 312 can provide fluid path 314 to facilitate the transport of a fluid through analysis zone 362. Analysis zone 362 can be proximate to a SOE, e.g., spherical lens element 360. Spherical lens element 360 can define a portion of a boundary of fluid path 314, e.g., spherical lens element 360 can act as part of the wall of a tunnel through FCD 312 that carries a flowing fluid. Fluid flow can be introduced to fluid path 314 as fluid flow to analysis zone 320. Fluid can flow from fluid flow to analysis zone 362 to fluid flow from analysis zone 340 via fluid path 314 and, as such, can transition through analysis zone 362.

In an aspect, spherical lens element 360 can enable optical energy 330 to be passed into and out of analysis zone 362 from outside of the fluid path. Whereas fluid flow to analysis zone 320 can be introduced through a sealed connection to a fluidic system and removed via fluid flow from analysis zone 340 can be similarly sealed to the fluidic system, spherical lens element 360 can provide for optical interrogation of an in situ sample at analysis zone 362 by an external optical analysis device. This can provide a seamless integration of the measurement interface into fluid path 314. In an aspect, spherical lens element 360 can be provided as a conduit to which removable optical analysis components, e.g., 150, etc., can be attached and detached from FCD 312.

In some embodiments, system 300 can facilitate additional interrogation of the fluid flowing in fluid path 314. FCD 312 can include additional fluid interrogation interface 370. As an example, additional fluid interrogation interface 370 can include or befitted with a reflector, substrate, etc., that can enhance or support an optical measurement via optical energy 330, e.g., a surface enhanced Raman spectroscopy (SERS) substrate, a mirror, a metal surface, etc., that can prevent the body of FCD 312 from contributing a Raman signal, for example, by obscuring the body of FCD 312 from being interrogated by optical energy 330. Further, additional fluid interrogation interface 370 can enable creation of a multivariate measurement location of the fluid at analysis zone 362 of fluid path 314 by providing access to the fluid. In some embodiments, additional fluid interrogation interface 370 can be proximate (e.g., adjacent) to the analysis zone, e.g., analysis zone 262, corresponding to spherical lens element 360. In other embodiments, additional fluid interrogation interface 370 need not be proximate to the analysis zone. In some embodiments, the additional fluid interrogation interface 370 may include a retroreflective surface that acts as a portion of the fluid path 314 and is located on the opposite side of the analysis zone 362 from the side of the analysis zone 362 where the spherical lens element 360 is located. The retroreflective surface of the additional fluid interrogation interface 370 may be an array of corner reflectors or a concave spherical surface. An example purpose of this retroreflective surface is to focus and return optical energy to the spherical lens element 360. The retroreflective surface of the additional fluid path interrogation interface 370 may be treated (e.g. electropolished) to enhance reflective efficiency. The retroreflective surface of the additional fluid path interrogation interface 370 may be permanently manufactured as part of the FCD 312 or removable (e.g. a threaded or press-fit insert with a retroreflective tip/surface). If the additional fluid path interrogation interface 370 is a retroreflective removable insert, the retroreflective removable insert may have a retroreflective surface as its tip and can be manually adjusted to move towards and away from the spherical lens element 360 to optimize the return of optical energy. The additional fluid path interrogation interface 370 implemented as a removable insert can be retained in the FCD 312 with any suitable corrosion-resistant and leak-resistant solution (i.e. so that fluid will not leak between the insert and the FCD 312 during medium pressure fluid flow). This can be achieved via press fit, adhesive bond, brazing, soldering, or threading.

In an aspect, FCD 312 can include, in some embodiments, sensor device(s) 380. Sensor device(s) 380 can include a sensor related to measuring temperature, pressure, flow, pH, salinity, turbidity, etc., of the flowing fluid, of FCD 312, of spherical lens element 360, etc. As an example, sensor device(s) 380 can include a pressure sensor before and after the analysis zone of fluid path 314, whereby the relative pressures of the fluid at these locations can indicate the direction of flow, speed of flow, viscosity of the fluid, etc., at the analysis zone. In an aspect, these example sensor device(s) 380 can be employed to trigger one or more optical analyses, e.g., the pressure differential can be used to determine a flow rate such that an optical analysis is triggered (e.g., when flow rate satisfies (e.g., meets or exceeds) a turbidity threshold) when the measurement would not be redundant as could occur for repeated measurements of a slow flowing fluid. As another example, a turbidity sensor can be employed to trigger an optical analysis when the flowing fluid becomes turbid, e.g., where the flowing fluid includes a carrier fluid with intermitted slugs of fluids of interest demarked by higher turbidity that the carrier fluid, the presence of a turbid region can trigger analysis to capture measurements of the fluid of interest as it passes through the analysis zone. Numerous other examples will be readily appreciated and all such examples are within the scope of the present disclosure despite not being expressly recited for the sake of clarity and brevity.

In an aspect, optical analysis via spherical lens element 360 can be correlated to interrogation results via additional fluid path interrogation interface 370 and/or measurements of sensor device(s) 380. This can provide additional analytical vectors into the properties of the fluid passing through fluid path 314, particularly as it passes through the analysis zone affiliated with spherical lens element 360. It will also be noted that the fluid path can take any form needed to provide for additional fluid path interrogation interface 370 and is expressly not constrained to the block cutout illustrated in system 300, which is used for simplicity of illustration.

Figure 4:
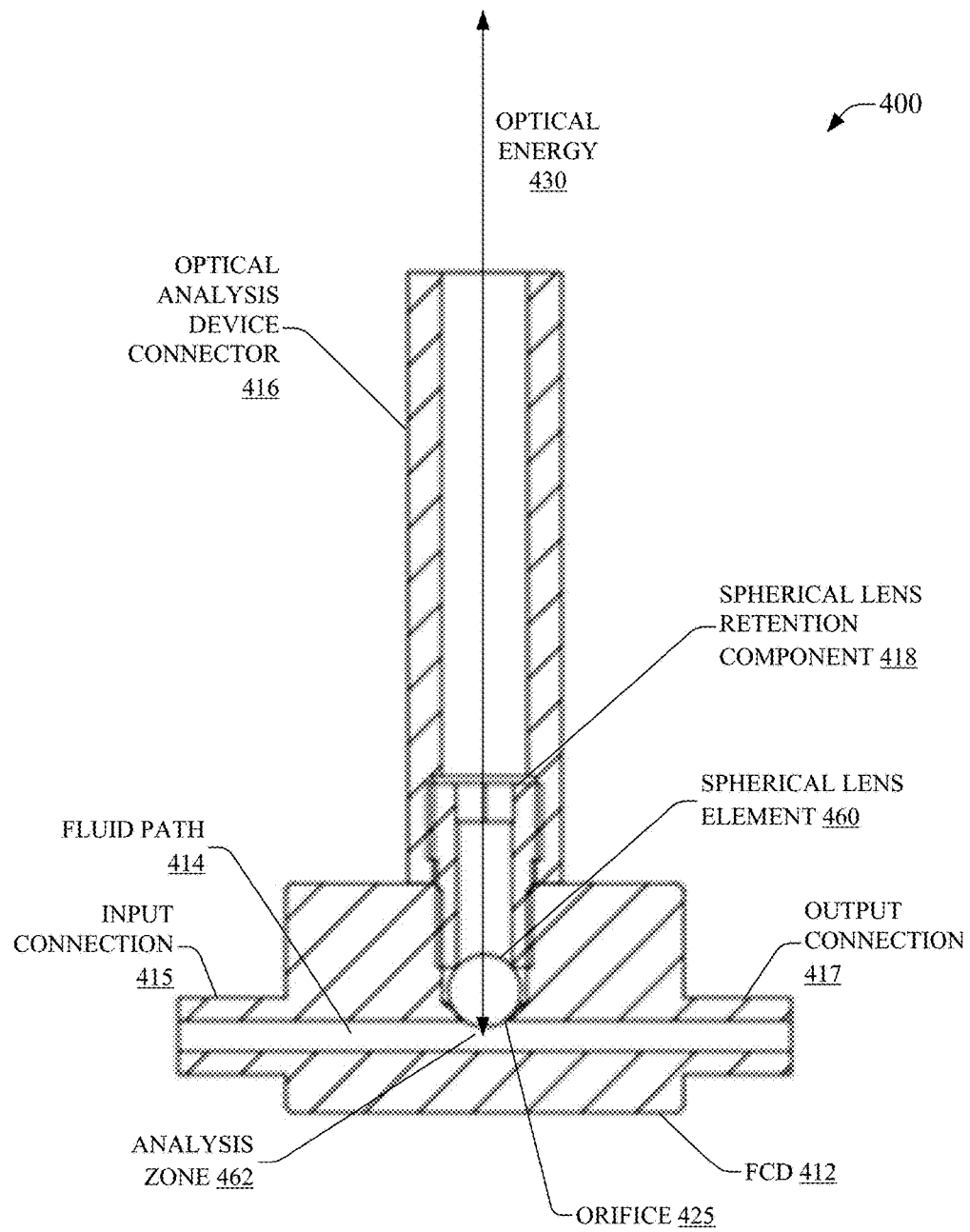
FIG. 4 is an illustration of a front cross-sectional view of an example system that can facilitate transmission of optical energy in and out of an analysis zone via a spherical optical element of flow cell device, wherein the spherical lens is sealed against an opening in a fluid path and is retained by a retention component, in accordance with aspects of the subject disclosure.

FIG. 4 is a front cross section illustration of a system 400, which can facilitate transmission of optical energy in and out of an analysis zone via a spherical optical element of flow cell device, wherein the spherical lens is sealed against an opening in a fluid path and is retained by a retention component, in accordance with aspects of the subject disclosure. System 400 can include flow cell device (FCD) 412. FCD 412 can provide fluid path 414 to facilitate the transport of a fluid through analysis zone 462. Analysis zone 462 can be proximate to a SOE, e.g., spherical lens element 460. Spherical lens element 460 can define a portion of a boundary of fluid path 414, e.g., spherical lens element 460 can act as part of the wall of a tunnel through FCD 412 that carries a flowing fluid. Spherical lens element 460 can be retained in FCD 412 via spherical lens retention component 418. Spherical lens retention component 418 can provide seating and sealing pressure, for example, via a threaded interface with FCD 412, via a friction fit interface with FCD 412, can be held in compression against the SOE by an adhesive bond to the body of FCD 412, can be brazed or soldered in place, etc. The spherical lens element 460 may, for example, be sealed into an orifice 425 that is defined in the flow cell device 412 at a portion of a boundary of the fluid path 414. In this manner, the spherical lens element 460 may provide optical access to the analysis zone 462 of the fluid path 414 while preventing leaking of the fluid between the spherical lens element 460 and the orifice 425.

FCD 412 can include an input connection 415 (e.g., a protrusion) that couples to an input connector of a fluidic system, and an output connection 417 (e.g., a protrusion) that couples to an output connector of a fluidic system. In some embodiments, the fluidic system can comprise a vessel, container, or the like that contains a fluid that can be expressed from the vessel, container, or the like. For example, in a medical setting, the input connection 415 may be configured to couple to a syringe (e.g., using a Luer lock fitting) that contains a fluid, and a human operator can physically express the fluid from the syringe into the fluid path 414. In some scenarios, FCD 412 may include the input connection 415 and may omit an output connection 417 so that FCD 412 can be filled with a fluid so that, once filled, optical interrogation of the fluid sample can commence. After completion of the optical interrogation, the fluid sample may egress from the fluid path 414 through the same point at which it entered the fluid path 414. Alternatively, the output connection 417 may be included, but sealed while FCD 412 is filled with a fluid sample. Additionally, or alternatively, FCD 412 may be disposable such that the human operator may dispose of FCD 412 after performing one or more optical interrogations of a fluid sample(s).

In an aspect, spherical lens element 460, via optical analysis device connector 416, can enable optical energy 430 to be passed into and out of analysis zone 462 from outside of the fluid path. Whereas fluid flow to analysis zone 462 can be introduced through sealed connections to a fluidic system, spherical lens element 460 can provide for optical interrogation of an in situ sample at analysis zone 462 by an external optical analysis device. This can provide a seamless integration of the measurement interface into fluid path 414. In an aspect, optical analysis device connector 416 can be a conduit (e.g., defined within a tube), and a removable optical analysis components, e.g., 150, etc., can be attached and detached from FCD 412 via the optical analysis device connector 416. In some, but not all, embodiments optical analysis device connector 416 can be cylindrically symmetric. Other embodiments can provide an optical path to/from spherical lens element 460 while having alternate geometries, e.g., a square cross section, an octagonal cross section, a cross section having a keyed portion to enable an addressable connection to an optical analysis component, e.g., optical analysis component 150, etc., or nearly any other shape that still provides an optical path for optical energy 430.

It is noted that system 400 is not illustrated in a proportionate manner and that the dimensions of the components illustrated can be other than illustrated without departing form the scope of the disclosed subject matter. As an example, spherical lens element 460 can be larger or smaller than illustrated in relation to fluid path 414. Moreover, the particular configuration of the illustrated components can be altered where the function of the components is retained. As examples, spherical lens retention component 418 can be reduced to fit entirely within FCD 412, optical analysis device connector 416 can be longer/shorter, have a thinner/thicker wall, can have a larger/smaller inner diameter, etc., optical analysis device connector 416 can be mounted into the body of FCD 412, can be adhered to, welded, braised, soldered, etc., to FCD 412, can include spherical lens retention component 418, FCD 412 can include optical analysis device connector 416, etc., without departing from the scope of the disclosed subject matter.

Figure 5:
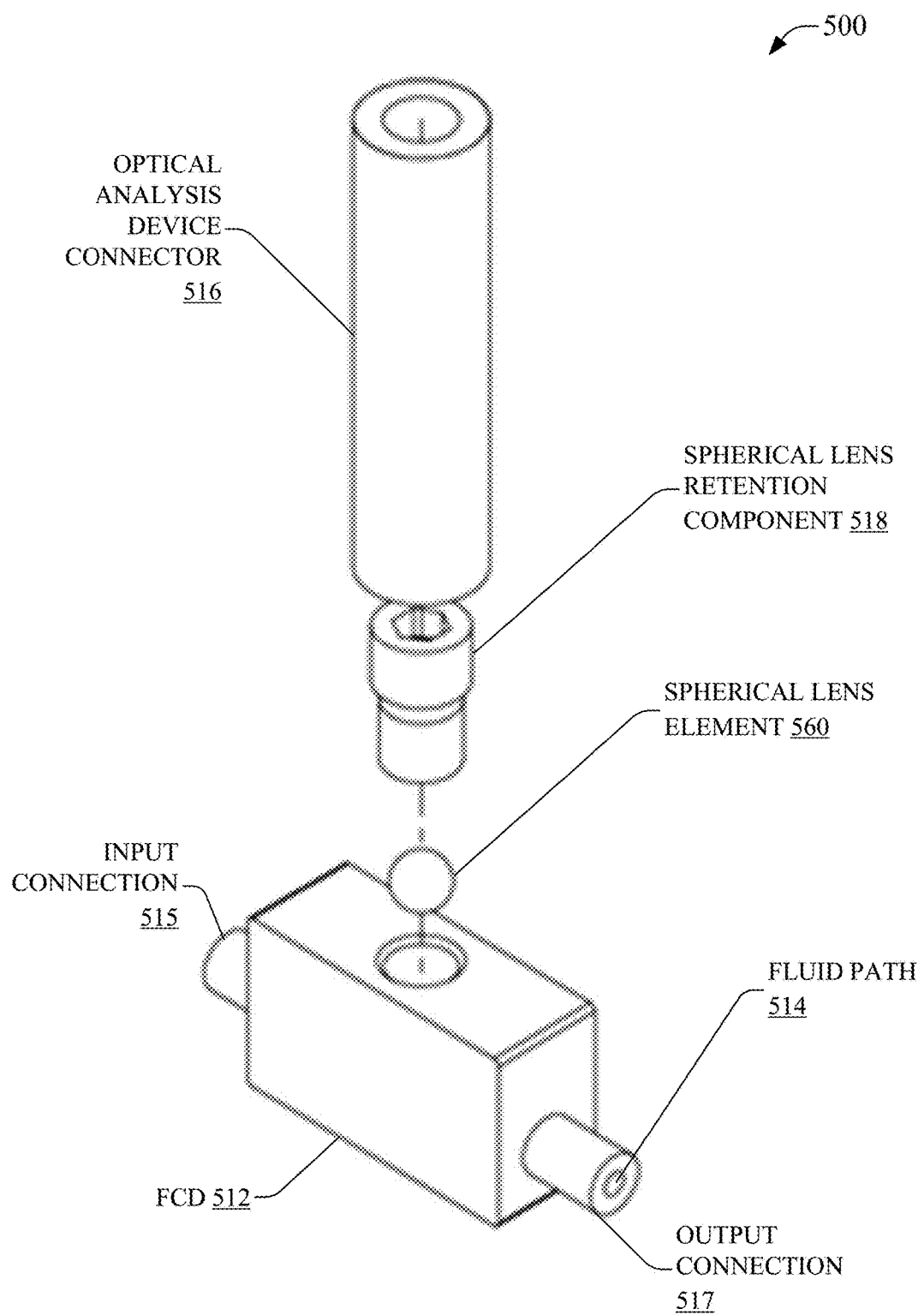
FIG. 5 is an illustration of a perspective exploded view of an example system including a spherical lens element that is retained via a retention component, in accordance with aspects of the subject disclosure.

FIG. 5 is an exploded view illustration of an example system 500 including a spherical lens element that is retained via a retention component, in accordance with aspects of the subject disclosure. Example system 500 can include FCD 512. FCD 512 can provide fluid path 514 to facilitate the transport of a fluid through a fluid analysis zone that can be proximate to a SOE, e.g., spherical lens element 560. Spherical lens element 560 can define a portion of a boundary of fluid path 514, e.g., spherical lens element 560 can act as part of the wall of a tunnel through FCD 512 that carries a flowing fluid. Spherical lens element 560 can be retained in FCD 512 via spherical lens retention component 518. Spherical lens retention component 518 can provide seating and sealing pressure, for example, via a threaded interface with FCD 512, via a friction fit interface with FCD 512, can be held in compression against the SOE by an adhesive bond to FCD 512, can be brazed or soldered in place, etc. FCD 512 can include an input connection 515 (e.g., a protrusion) that couples to an input connector of a fluidic system, and an output connection 517 (e.g., a protrusion) that couples to an output connector of a fluidic system.

In an aspect, spherical lens element 560 can enable optical energy to be passed into and out of the analysis zone from outside of the fluid path via optical analysis device connector 516. Whereas fluid flow to the analysis zone can be introduced through sealed connections to a fluidic system, spherical lens element 560 can provide for optical interrogation of an in situ sample at the analysis zone by an external optical analysis device. This can provide a seamless integration of the measurement interface into fluid path 514. In an aspect, optical analysis device connector 516 can be a conduit (e.g., defined within a tube), and a removable optical analysis components, e.g., optical analysis components 150, etc., can be attached and detached from FCD 512 via the optical analysis device connector 516. In some, but not all, embodiments optical analysis device connector 516 can be cylindrically symmetric. Optical analysis device connector 516 can include a fitting component, an indexing component, etc., e.g. can be tapered, keyed, etc., on the interface, etc. Other embodiments can provide an optical path to/from spherical lens element 560 while having alternate geometries.

Some embodiments of the disclosed subject matter can include a spherical lens element 560 included of glass, doped glass, sapphire, diamond, ruby, zinc selenide, potassium bromide crystal, sodium bromide crystal, polymer, etc. Some embodiments of the disclosed subject matter can include a FCD 512 included of a metal, alloy, polymer, ceramic, composite, glass, etc. Some embodiments of the disclosed subject matter can include a seal between the FCD 512 and spherical lens element 560 that is a compression seal, epoxy seal, etc. Some embodiments of the disclosed subject matter can include an attachment between the optical analysis device connector 516 and an optical analysis component 150 that is permanent, removable, etc. Some embodiments of the disclosed subject matter can include a fluid path 514 that can be diverted internally to accommodate an additional measurement port, e.g., additional fluid path interrogation interface 370, 670, etc., sensor device(s) 380, etc., or other fluid interactions and/or reactions. Some embodiments of the disclosed subject matter can include a fluid paths 514 that can be manipulated internally, e.g., filtering, injection, cooling/heating, etc., in combination with spectroscopic measurement.

Figure 6:
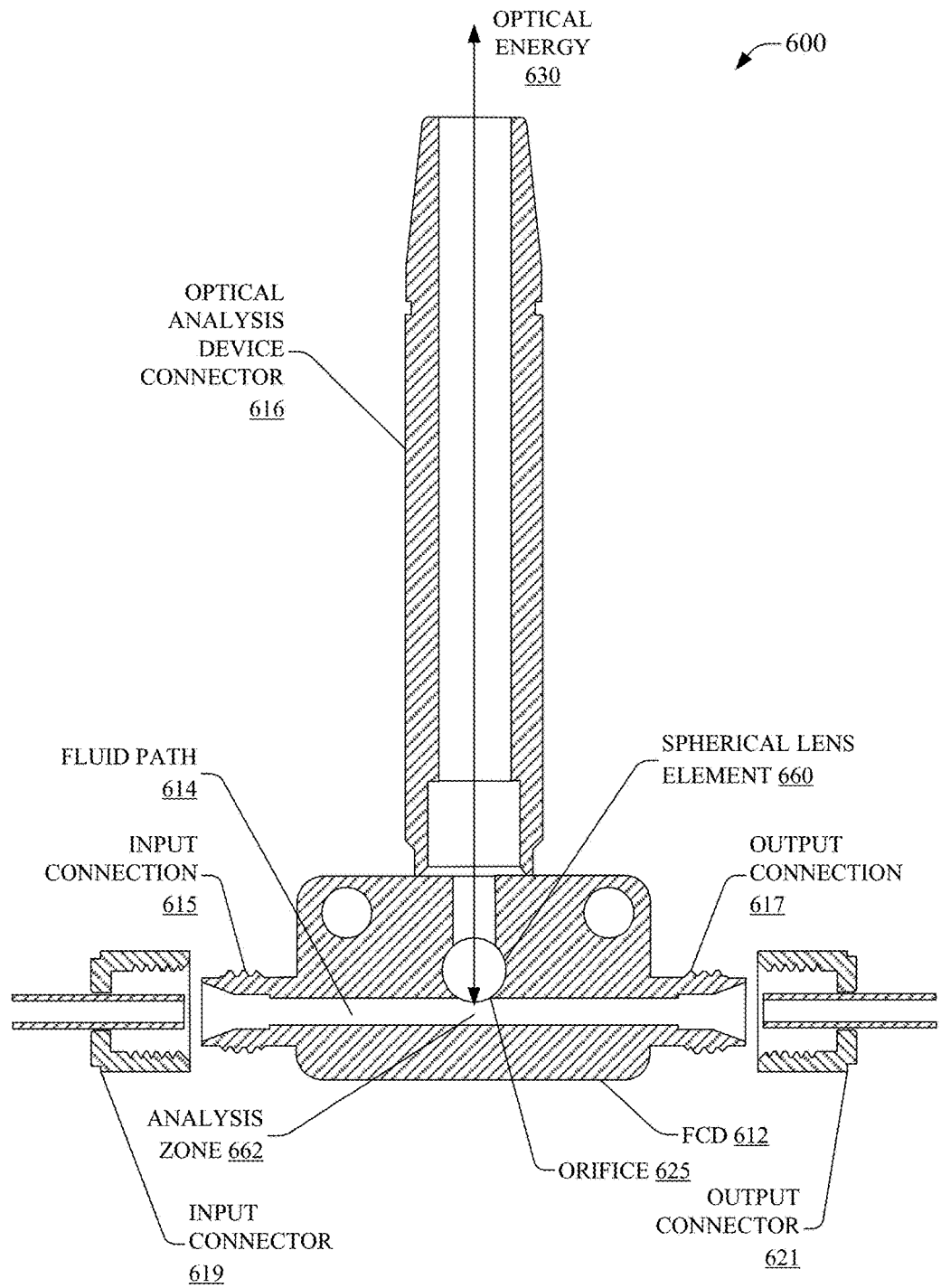
FIG. 6 is an illustration of a front cross-sectional view of an example system that can facilitate transmission of optical energy in and out of an analysis zone via a spherical optical element of flow cell device, in accordance with aspects of the subject disclosure.

FIG. 6 is a front cross section illustration of a system 600, which can facilitate transmission of optical energy in and out of an analysis zone via a spherical optical element of flow cell device, in accordance with aspects of the subject disclosure. System 600 can include flow cell device (FCD) 612. FCD 612 may be a low-pressure flow cell device suitable for use with low pressure fluidic systems (e.g., in a range from 0 to approximately 500 pounds per square inch (psi)). The FCD 612 can provide fluid path 614 to facilitate the transport of a fluid through analysis zone 662. Analysis zone 662 can be proximate to a SOE, e.g., spherical lens element 660. Spherical lens element 660 can define a portion of a boundary of fluid path 614, e.g., spherical lens element 660 can act as part of the wall of a tunnel through FCD 612 that carries a flowing fluid. Spherical lens element 660 can be retained in FCD 612 via a spherical lens retention component, in some embodiments, which may provide seating and sealing pressure against the spherical lens element 660. Spherical lens element 660 may, alternatively, be held in place by an adhesive bond to the body of FCD 612, and/or the spherical lens element 660 can be brazed or soldered in place, and/or an elastomer seal may be provided, etc. The spherical lens element 660 may, for example, be sealed into an orifice 625 that is defined in the flow cell device 612 at a portion of a boundary of the fluid path 614. In this manner, the spherical lens element 660 may provide optical access to the analysis zone 662 of the fluid path 614 while preventing leaking of the fluid between the spherical lens element 660 and the orifice 625.

FCD 612 can include an input connection 615 (e.g., an externally threaded protrusion) that couples to an input connector 619 of a fluidic system, and an output connection 617 (e.g., an externally threaded protrusion) that couples to an output connector 621 of a fluidic system. In some embodiments, the fluidic system can comprise a vessel, container, or the like that contains a fluid that can be expressed from the vessel, container, or the like. For example, in a medical setting, the input connection 615 may be configured to couple to a syringe (e.g., using a Luer lock fitting) that contains a fluid, and a human operator can physically express the fluid from the syringe into the fluid path 614. In some scenarios, FCD 612 may include the input connection 615 and may omit an output connection 617 so that FCD 612 can be filled with a fluid so that, once filled, optical interrogation of the fluid sample can commence. After completion of the optical interrogation, the fluid sample may egress from the fluid path 614 through the same point at which it entered the fluid path 614. Alternatively, the output connection 617 may be included, but sealed while FCD 612 is filled with a fluid sample. Additionally, or alternatively, FCD 612 may be disposable such that the human operator may dispose of FCD 612 after performing one or more optical interrogations of a fluid sample(s).

In an aspect, spherical lens element 660, via optical analysis device connector 616, can enable optical energy 630 to be passed into and out of analysis zone 662 from outside of the fluid path. Whereas fluid flow to analysis zone 662 can be introduced through sealed connections to a fluidic system, spherical lens element 660 can provide for optical interrogation of an in situ sample at analysis zone 662 by an external optical analysis device. This can provide a seamless integration of the measurement interface into fluid path 614. In an aspect, optical analysis device connector 616 can be a conduit (e.g., defined within a tube), and a removable optical analysis component, e.g., 150, etc., can be attached and detached from FCD 612 via the optical analysis device connector 616. Optical analysis device connector 616 can be attached to the body of FCD 612 in any suitable manner, such as a weld, a threaded coupling, or any suitable form of attachment. In some, but not all, embodiments optical analysis device connector 616 can be cylindrically symmetric. Other embodiments can provide an optical path to/from spherical lens element 660 while having alternate geometries, e.g., a square cross section, an octagonal cross section, a cross section having a keyed portion to enable an addressable connection to an optical analysis component, e.g., optical analysis component 150, etc., or nearly any other shape that still provides an optical path for optical energy 630.

It is noted that system 600 is not illustrated in a proportionate manner and that the dimensions of the components illustrated can be other than illustrated without departing from the scope of the disclosed subject matter. As an example, spherical lens element 660 can be larger or smaller than illustrated in relation to fluid path 614. Moreover, the particular configuration of the illustrated components can be altered where the function of the components is retained. As examples, spherical lens retention component 618 can be reduced to fit entirely within FCD 612, optical analysis device connector 616 can be longer/shorter, have a thinner/thicker wall, can have a larger/smaller inner diameter, etc., optical analysis device connector 616 can be mounted into the body of FCD 612, can be adhered to, welded, braised, soldered, etc., to FCD 612, can include spherical lens retention component 618, FCD 612 can include optical analysis device connector 616, etc., without departing from the scope of the disclosed subject matter.

Figure 7:
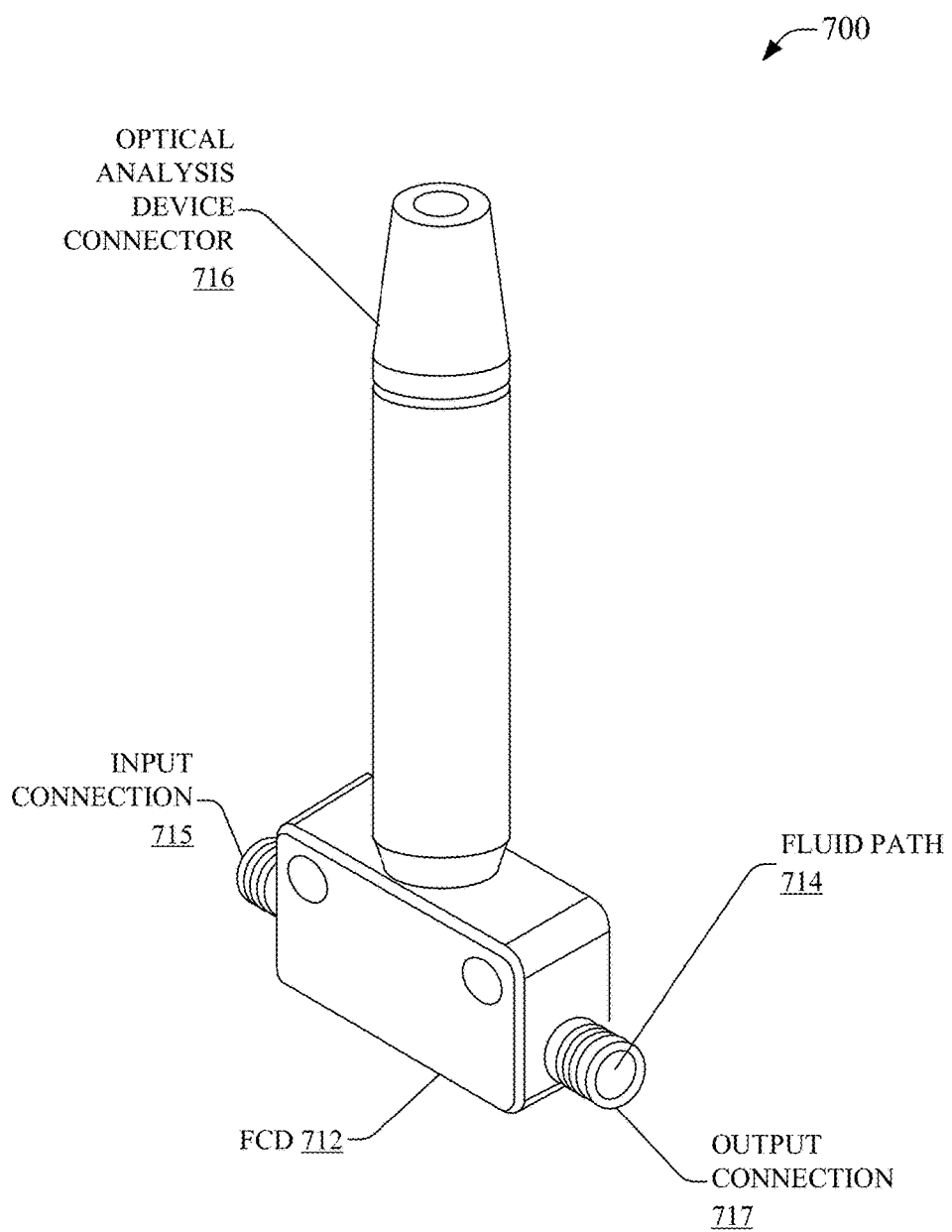
FIG. 7 is an illustration of a perspective view of an example system similar to the system of FIG. 6.

FIG. 7 is an illustration of a perspective view of an example system 700 similar to the system 600 of FIG. 6. The system 700 may include the same or similar components to those described with reference to FIG. 6, including, as shown in FIG. 7, a FCD 712 having an input connection 715, an output connection 717, and a fluid path 714 defined therein, as well as an optical analysis device connector 716.

Figure 8:
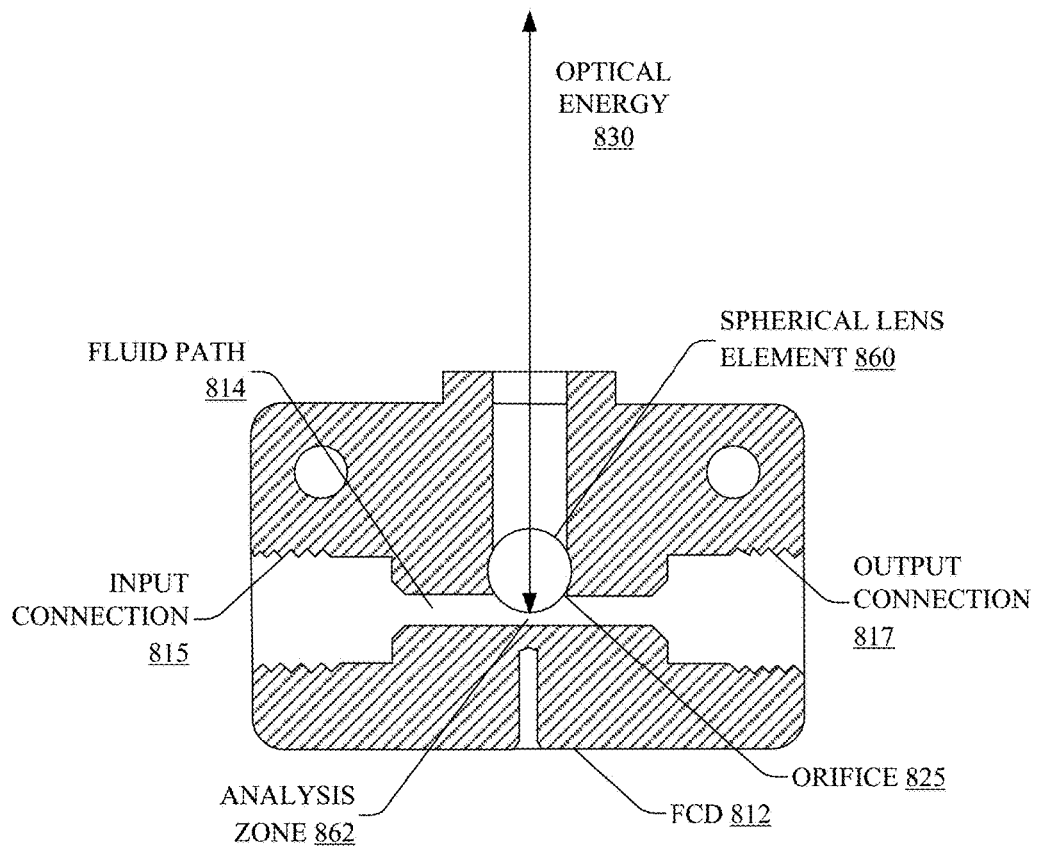
FIG. 8 is an illustration of a front cross-sectional view of an example flow cell device, in accordance with aspects of the subject disclosure.

FIG. 8 is a front cross section illustration of an example flow cell device 812, in accordance with aspects of the subject disclosure. FCD 812 may be a medium-pressure flow cell device suitable for use with medium pressure fluidic systems (e.g., in a range from about 500 psi to about 2500 psi). The FCD 812 can provide fluid path 814 to facilitate the transport of a fluid through analysis zone 862. Analysis zone 862 can be proximate to a SOE, e.g., spherical lens element 860. Spherical lens element 860 can define a portion of a boundary of fluid path 814, e.g., spherical lens element 860 can act as part of the wall of a tunnel through FCD 812 that carries a flowing fluid. Spherical lens element 860 can be retained in FCD 812 via any suitable mechanism, such as a press fit, an adhesive bond, brazing, soldering, etc. The spherical lens element 860 may, for example, be sealed into an orifice 825 that is defined in the flow cell device 812 at a portion of a boundary of the fluid path 814. In this manner, the spherical lens element 860 may provide optical access to the analysis zone 862 of the fluid path 814 while preventing leaking of the fluid between the spherical lens element 860 and the orifice 825.

FCD 812 can include an input connection 815 (e.g., an internally threaded hole) that couples to (e.g., by receiving) an input connector of a fluidic system, and an output connection 817 (e.g., an internally threaded hole) that couples to (e.g., by receiving) an output connector of a fluidic system. In some embodiments, the fluidic system can comprise a vessel, container, or the like that contains a fluid that can be expressed from the vessel, container, or the like. For example, in a medical setting, the input connection 815 may be configured to couple to a syringe (e.g., using a Luer lock fitting) that contains a fluid, and a human operator can physically express the fluid from the syringe into the fluid path 814. In some scenarios, FCD 812 may include the input connection 815 and may omit an output connection 817 so that FCD 812 can be filled with a fluid so that, once filled, optical interrogation of the fluid sample can commence. After completion of the optical interrogation, the fluid sample may egress from the fluid path 814 through the same point at which it entered the fluid path 814. Alternatively, the output connection 817 may be included, but sealed while FCD 812 is filled with a fluid sample. Additionally, or alternatively, FCD 812 may be disposable such that the human operator may dispose of FCD 812 after performing one or more optical interrogations of a fluid sample(s). In a similar scenario, the output connection (817, for example) may be connected directly to a locked/secured biological waste container (e.g. via a tamper-evident seal or a cap with a lock). Once a human operator physically expresses fluid from a syringe into the fluid path 814, the fluid cannot be diverted before being rendered unrecoverable (either physically and/or chemically) by the waste container. An optional and additional output connection may exist on the FCD 812 to provide an option for fluid recovery after optical interrogation but before dispensing into a secure waste container (i.e. before the fluid is rendered unrecoverable).

In an aspect, spherical lens element 860, via an optical analysis device connector, can enable optical energy 830 to be passed into and out of analysis zone 862 from outside of the fluid path. Whereas fluid flow to analysis zone 862 can be introduced through sealed connections to a fluidic system, spherical lens element 860 can provide for optical interrogation of an in situ sample at analysis zone 862 by an external optical analysis device. This can provide a seamless integration of the measurement interface into fluid path 814.

It is noted that FCD 812 is not illustrated in a proportionate manner and that the dimensions of the components illustrated can be other than illustrated without departing form the scope of the disclosed subject matter. As an example, spherical lens element 860 can be larger or smaller than illustrated in relation to fluid path 814. Moreover, the particular configuration of the illustrated components can be altered where the function of the components is retained.

Figure 9:
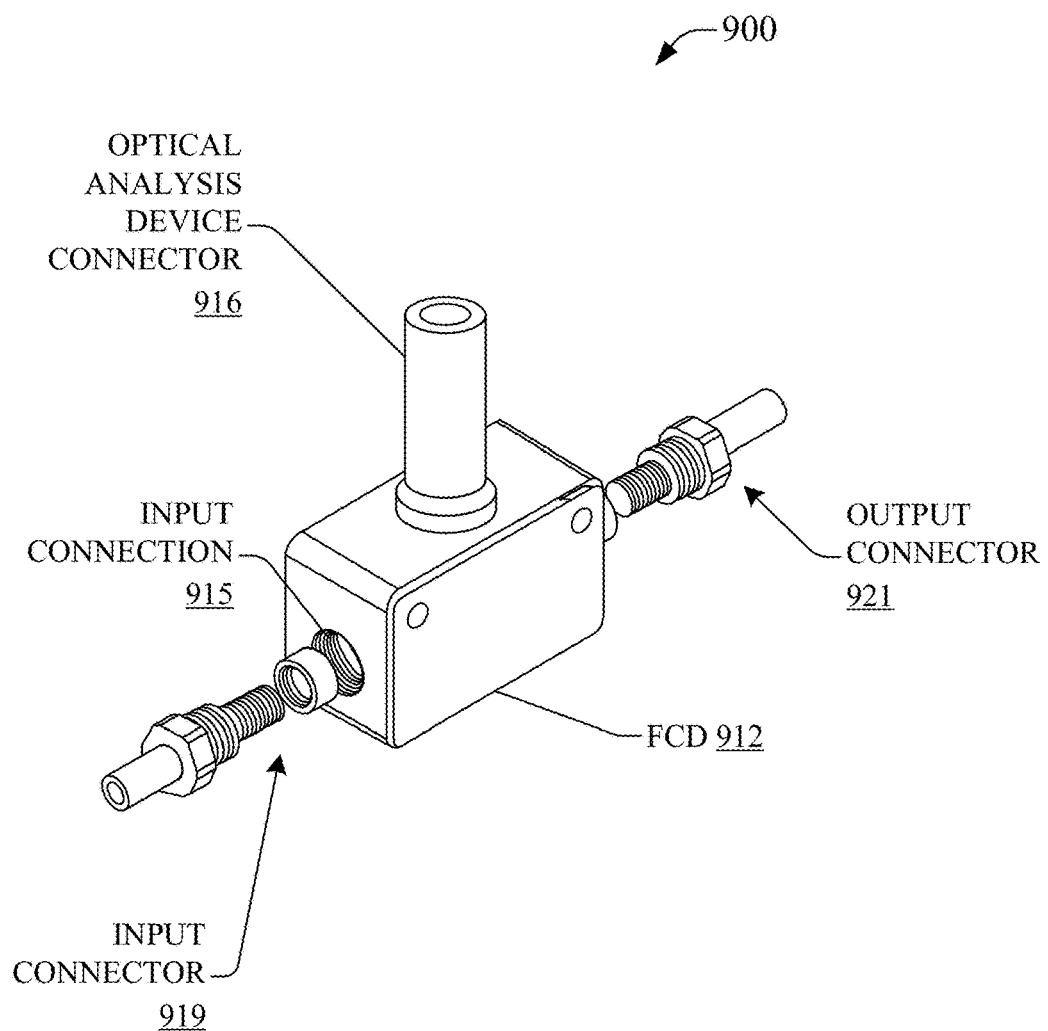
FIG. 9 is an illustration of a perspective partially exploded view of an example system with a flow cell device similar to the flow cell device of FIG. 8.

FIG. 9 is an illustration of a perspective view of an example system 900 with a flow cell device 912 similar to the flow cell device 812 of FIG. 8. The system 900 may include the same or similar components to those described with reference to FIG. 8, including, as shown in FIG. 9, a FCD 912 having an input connection 915. In addition, the system 900 shown in FIG. 9 includes an input connector 919 and an output connector 921 configured to couple to the input connection 915 and the output connection (e.g., output connection 817 of FIG. 8), respectively. These input/output connectors 919/921 may, for example, include external threads, and possibly multiple components to threadingly couple with the FCD 912 to create a sealed fluid path (e.g., fluid path 814 of FIG. 8). The system 900 may also include an optical analysis device connector 916. In an aspect, optical analysis device connector 916 can be a conduit (e.g., defined within a tube), and a removable optical analysis components, e.g., 150, etc., can be attached and detached from FCD 912 via the optical analysis device connector 916. In some, but not all, embodiments optical analysis device connector 916 can be cylindrically symmetric. Other embodiments can provide an optical path to/from spherical lens element (e.g., spherical lens element 860 of FIG. 8) while having alternate geometries, e.g., a square cross section, an octagonal cross section, a cross section having a keyed portion to enable an addressable connection to an optical analysis component, e.g., optical analysis component 150, etc., or nearly any other shape that still provides an optical path for optical energy 830. As examples, optical analysis device connector 916 can be mounted into the body of FCD 812, can be adhered to, welded, braised, soldered, etc., to FCD 812, without departing from the scope of the disclosed subject matter.

Figure 10:
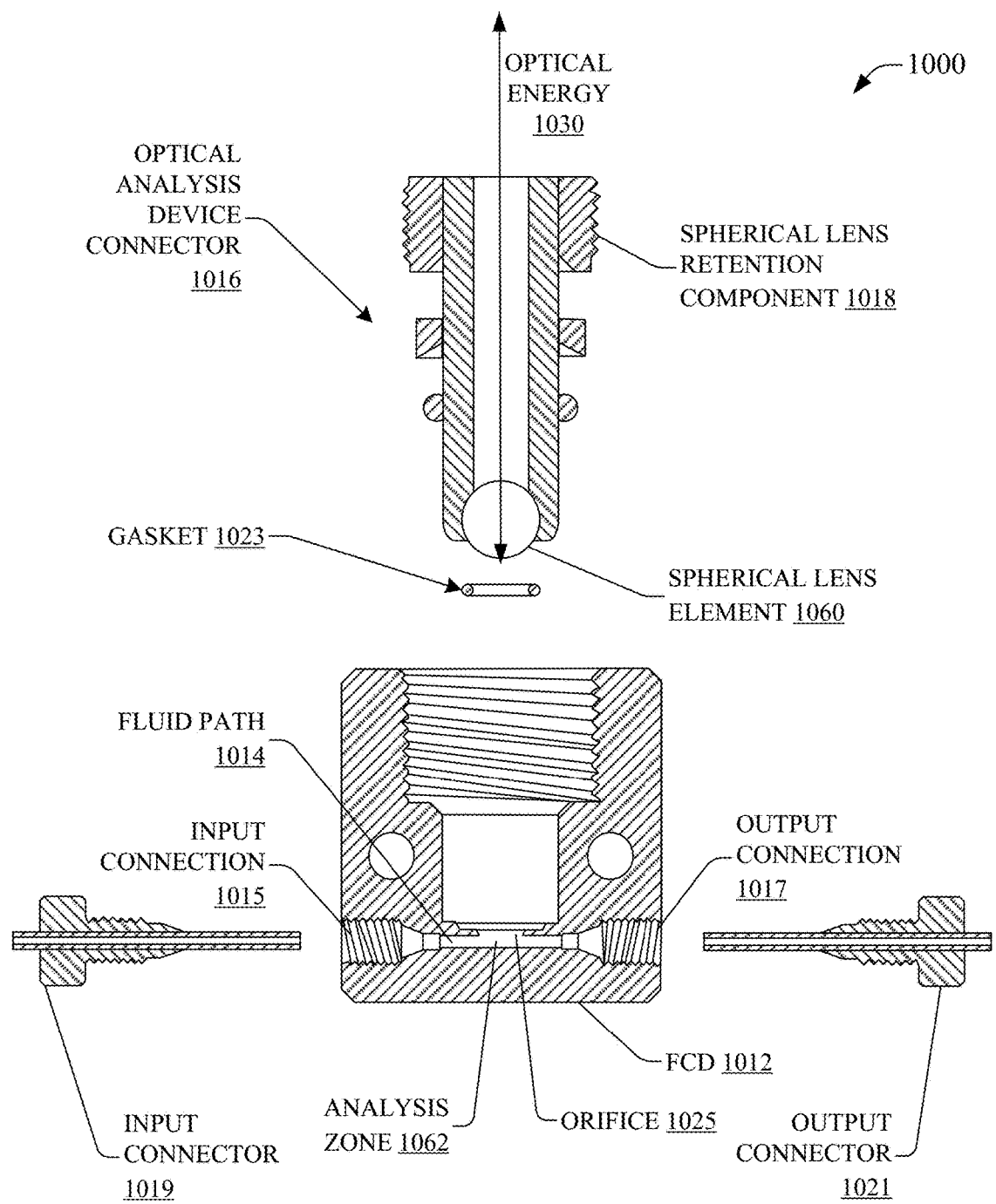
FIG. 10 is an illustration of a front exploded cross-sectional view of an example system that can facilitate transmission of optical energy in and out of an analysis zone via a spherical optical element of flow cell device, in accordance with aspects of the subject disclosure.
Figure 11:
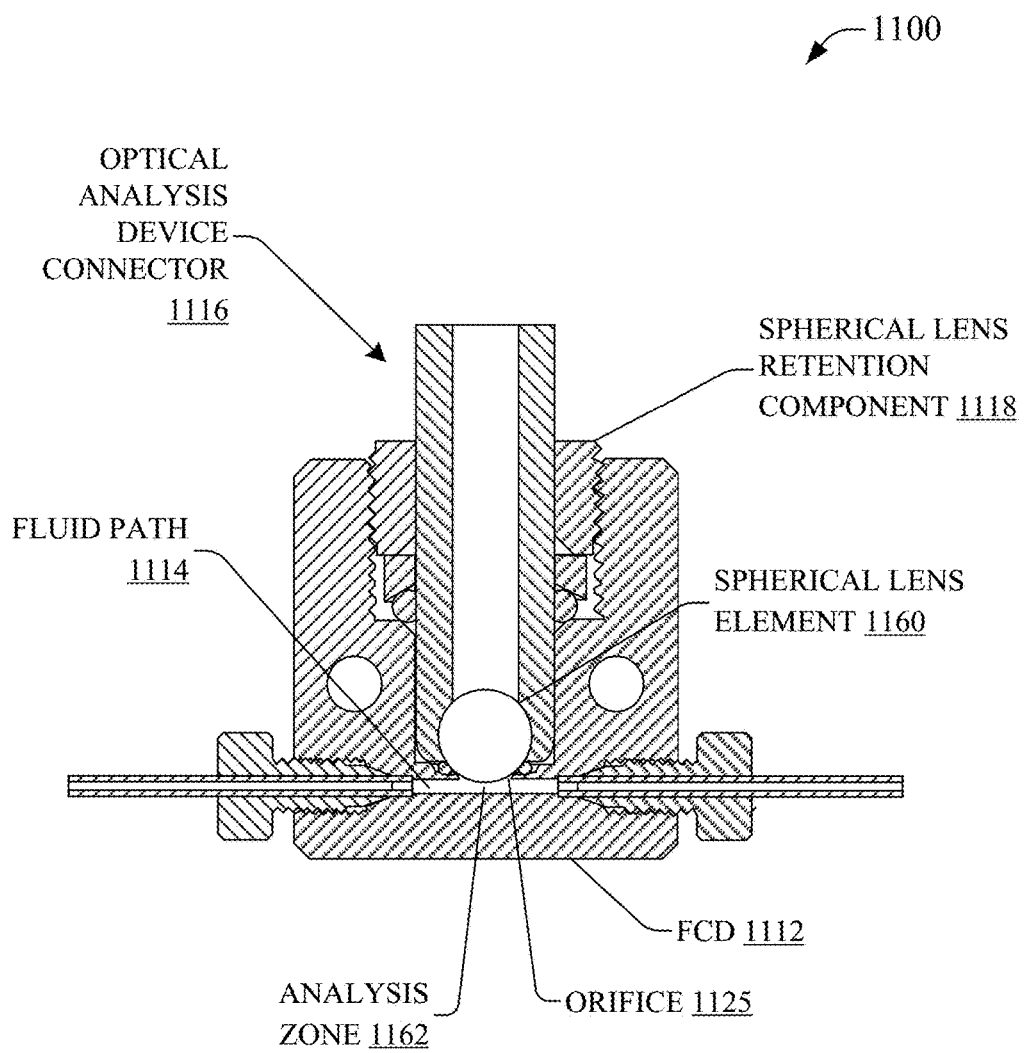
FIG. 11 is an illustration of a front cross-sectional view of the example system of FIG. 10.

FIG. 10 is a front cross section illustration of a system 1000, which can facilitate transmission of optical energy in and out of an analysis zone via a spherical optical element of flow cell device, in accordance with aspects of the subject disclosure. System 1000 can include flow cell device (FCD) 1012. FCD 1012 may be configured for use with an autoclavable biotech Raman BallProbe, such as the Marqmetrix BioReactor BallProbe, a Raman probe with an ability to effectively withstand harsh effects of an apparatus used in a sterilizing process through the application of high heat and pressure. The FCD 1012 can provide fluid path 1014 to facilitate the transport of a fluid through analysis zone 1062. Analysis zone 1062 can be proximate to a SOE, e.g., spherical lens element 1060, as is shown in FIG. 11 with the non-exploded cross-sectional view of the system 1100, which may be the same system or a similar system to the system 1000, including an analysis zone 1162 and a spherical lens element 1160. Spherical lens element 1060 can define a portion of a boundary of fluid path 1014, e.g., spherical lens element 1060 can act as part of the wall of a tunnel through FCD 1012 that carries a flowing fluid. Spherical lens element 1060 can be retained in FCD 1012 via spherical lens retention component 1018. Spherical lens retention component 1018 can provide seating and sealing pressure, for example, via a threaded interface with FCD 1012, via a friction fit interface with FCD 1012, can be held in compression against the SOE by an adhesive bond to the body of FCD 1012, can be brazed or soldered in place, etc. The spherical lens element 1060/1160 may, for example, be sealed into an orifice 1025/1125 (as shown in FIG. 11), the orifice 1025/1125 defined in the flow cell device 1012/1112 at a portion of a boundary of the fluid path 1014/1114. FIG. 10 shows a gasket 1023 (e.g., a rubber gasket, an elastomer gasket, an epoxy gasket, a deformable metal (e.g., gold) gasket, etc.) that may provide such a seal between the spherical lens element 1060/1160 and the orifice 1025/1125 into the fluid path 1014/1114. In this manner, the spherical lens element 1060/1160 may provide optical access to the analysis zone 1062/1162 of the fluid path 1014/1114 while preventing leaking of the fluid between the spherical lens element 1060/1160 and the orifice 1025/1125 (when in the configuration of FIG. 11). Alternatively, spherical lens element 1060 may be mounted in the body of FCD 1012 without spherical lens retention component 1018. FCD 1012 can include an input connection 1015 (e.g., an internally threaded hole) that couples to an input connector 1019 of a fluidic system, and an output connection 1017 (e.g., an internally threaded hole) that couples to an output connector 1021 of a fluidic system. In some embodiments, the fluidic system can comprise a vessel, container, or the like that contains a fluid that can be expressed from the vessel, container, or the like. For example, in a medical setting, the input connection 1015 may be configured to couple to a syringe (e.g., using a Luer lock fitting) that contains a fluid, and a human operator can physically express the fluid from the syringe into the fluid path 1014. In some scenarios, FCD 1012 may include the input connection 1015 and may omit an output connection 1017 so that FCD 1012 can be filled with a fluid so that, once filled, optical interrogation of the fluid sample can commence. After completion of the optical interrogation, the fluid sample may egress from the fluid path 1014 through the same point at which it entered the fluid path 1014. Alternatively, the output connection 1017 may be included, but sealed while FCD 1012 is filled with a fluid sample. Additionally, or alternatively, FCD 1012 may be disposable such that the human operator may dispose of FCD 1012 after performing one or more optical interrogations of a fluid sample(s).

In an aspect, spherical lens element 1060, via optical analysis device connector 1016, can enable optical energy 1030 to be passed into and out of analysis zone 1062 from outside of the fluid path. Whereas fluid flow to analysis zone 1062 can be introduced through sealed connections to a fluidic system, spherical lens element 1060 can provide for optical interrogation of an in situ sample at analysis zone 1062 by an external optical analysis device. This can provide a seamless integration of the measurement interface into fluid path 1014. In an aspect, optical analysis device connector 1016 can be a conduit (e.g., defined within a tube), and a removable optical analysis components, e.g., 150, etc., can be attached and detached from FCD 1012 via the optical analysis device connector 1016. In some, but not all, embodiments optical analysis device connector 1016 can be cylindrically symmetric. Other embodiments can provide an optical path to/from spherical lens element 1060 while having alternate geometries, e.g., a square cross section, an octagonal cross section, a cross section having a keyed portion to enable an addressable connection to an optical analysis component, e.g., optical analysis component 150, etc., or nearly any other shape that still provides an optical path for optical energy 1030.

It is noted that system 1000 and the system 1100 are not illustrated in a proportionate manner and that the dimensions of the components illustrated can be other than illustrated without departing form the scope of the disclosed subject matter. As an example, spherical lens element 1060/1160 can be larger or smaller than illustrated in relation to fluid path 1014/1114. Moreover, the particular configuration of the illustrated components can be altered where the function of the components is retained. As examples, spherical lens retention component 1018/1118 can be reduced to fit entirely within FCD 1012/1112, optical analysis device connector 1016/1116 can be longer/shorter, have a thinner/thicker wall, can have a larger/smaller inner diameter, etc., optical analysis device connector 1016/1116 can be mounted into the body of FCD 1012/1112, can be adhered to, epoxied, welded, braised, soldered, etc., to FCD 1012/1112, can include spherical lens retention component 1018/1118, FCD 1012/1112 can include optical analysis device connector 1016/1116, etc., without departing from the scope of the disclosed subject matter.

Figure 12:
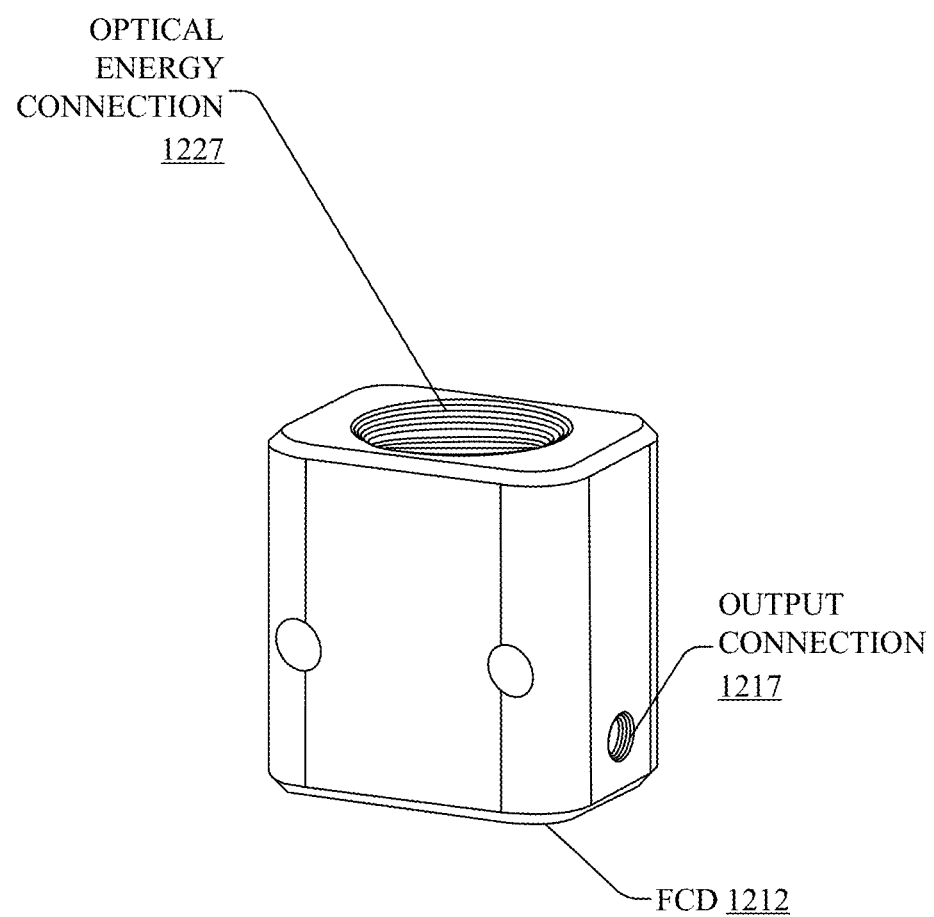
FIG. 12 is an illustration of a perspective view of an example flow cell device similar to the flow cell device of FIGS. 10 and 11.

FIG. 12 is an illustration of a perspective view of an example flow cell device 1212 similar to the flow cell device of FIGS. 10 and 11. The flow cell device 1212 may have similar features to the flow cell devices 1012 and 1112 of FIGS. 10 and 11, such as the features shown in FIG. 12, including the output connection 1217, and an optical energy connection 1227 to receive an optical analysis device connector 1016/1116 and a spherical lens retention component 1018/1118. The optical energy connection 1227 may be configured to couple FCD 1212 to an autoclavable biotech Raman BallProbe that is particularly tailored for use in bioprocess and/or sterile applications, such as the Marqmetrix BioReactor BallProbe. Accordingly, the optical analysis device connector 1016/1116 can represent a component part of an immersion probe that couples to FCD 1212 via the optical energy connection 1227.

Figure 13:
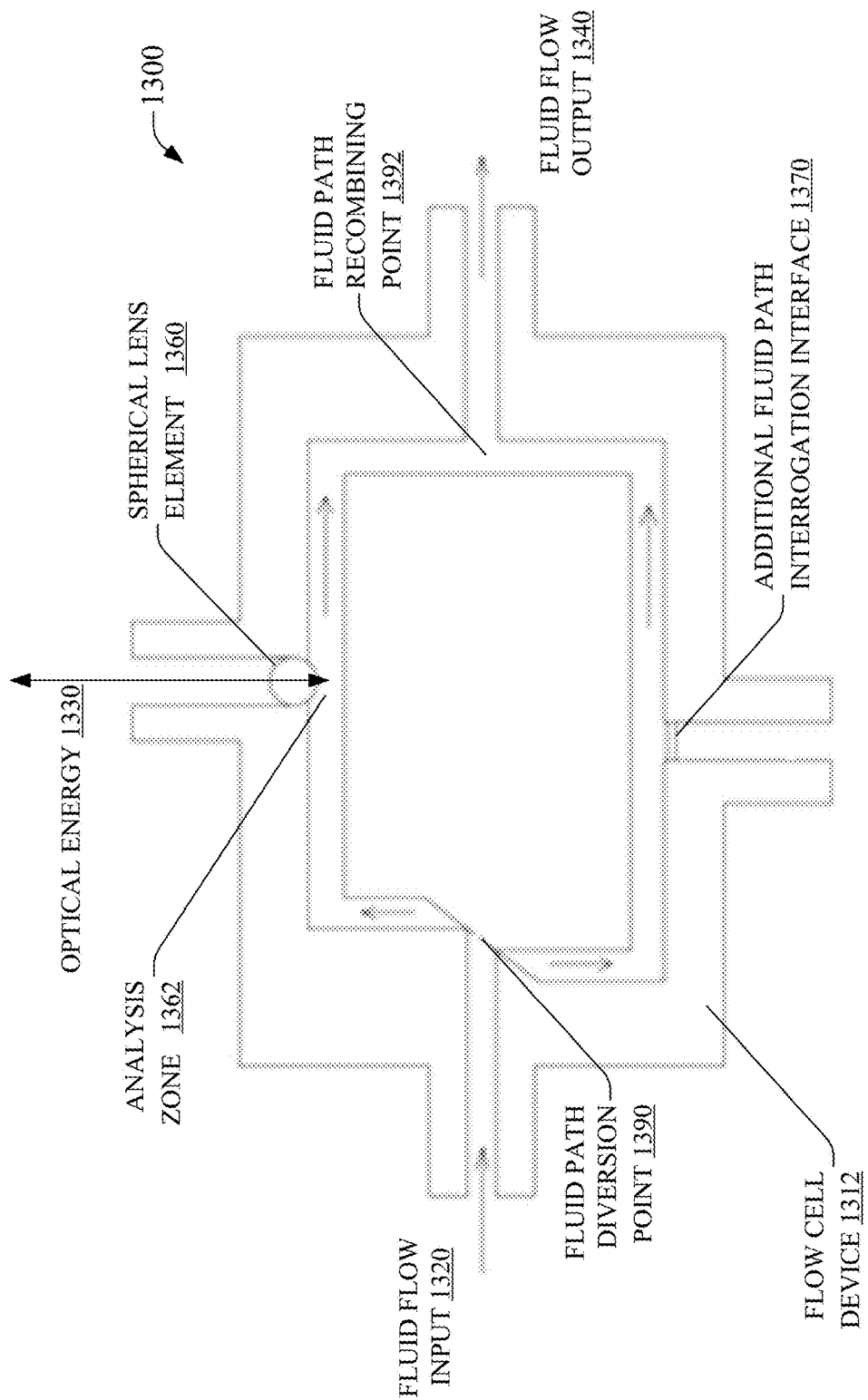
FIG. 13 is a cross section illustration of an example system that can facilitate transmitting optical energy in and out of an analysis zone via a spherical optical element of a first leg of a fluid path of a flow cell device and provides a second leg of the fluid path including an additional interrogation interface, in accordance with aspects of the subject disclosure.

FIG. 13 is a cross sectional illustration of a system 1300, which can facilitate transmitting optical energy in and out of an analysis zone via a spherical optical element of a first leg of a fluid path of a flow cell device and provides a second leg of the fluid path including an additional interrogation interface, in accordance with aspects of the subject disclosure. System 1300 can include flow cell device (FCD) 1312. FCD 1312 can provide a fluid path from fluid flow input 1320 to fluid flow output 1340. A portion of the fluid path can transport a fluid through analysis zone 1362. Analysis zone 1362 can be proximate to a SOE, e.g., spherical lens element 1360. Spherical lens element 1360 can define a portion of a boundary of the fluid path proximate to analysis zone 1362, e.g., spherical lens element 1360 can act as part of the wall of a tunnel through FCD 1312 that carries a flowing fluid.

In an aspect, spherical lens element 1360 can enable optical energy 1330 to be passed into and out of analysis zone 1362 from outside of the fluid path. Whereas fluid flow to analysis zone 1362 can be introduced through sealed connections to a fluidic system, spherical lens element 1360 can provide for optical interrogation of an in situ sample at analysis zone 1362 by an external optical analysis device. This can provide a seamless integration of the measurement interface into fluid path.

In some embodiments, system 1300 can facilitate additional interrogation of the fluid flowing in the fluid path. FCD 1312 can include additional fluid path interrogation interface 1370. Additional fluid path interrogation interface 1370 can enable creation of a multivariate measurement location of the fluid flowing through a corresponding portion of the fluid path. In some embodiments, additional fluid path interrogation interface 1370 can be proximate to the analysis zone, e.g., analysis zone 262, corresponding to spherical lens element 1360. In other embodiments, additional fluid interrogation interface 1370 need not be proximate to the analysis zone. It is noted that that the geometry of the fluid path can be determined to provide a known correlation between the fluid flowing at analysis zone 1362 and the fluid flowing at additional fluid path interrogation interface 1370 in view of the fluid path diversion point 1390. In some embodiments, fluid path diversion point 1390 can include, for example, a filter, selective membrane, passive valve, active valve, etc. Moreover, additional chemical interactions can be conducted on the fluid flowing via one or more portions of the fluid path. As an example, a pH indicator can be added to the fluid flowing past additional fluid path interrogation interface 1370, which can be correlated to the optical analysis of the fluid flowing past analysis zone 1362, such that the pH of the fluid can be correlated to the optical analysis of the fluid. The fluids can, in some embodiments be recombined at fluid path recombining point 1392. It will also be noted that the volumes of different portions of the flow path can be the same or different. As an example, 99.9% of the fluid can flow past analysis zone 1362 while 0.1% of the fluid flows past additional fluid path interrogation interface 1370. This example can allow the introduction of a pH indicator to the fluid flowing past additional fluid path interrogation interface 1370. This portion can then be discarded rather than being recombined at fluid path recombining point 1392. Additionally, there can be any number of additional fluid path interrogation interfaces and corresponding fluid path portions, without departing from the scope of the present disclosure, so as to allow for additional chemistry and/or fluid analysis before recombining some, all, or none of the additional fluid path interrogation interface fluid paths at fluid path recombining point 1392.

In an aspect, optical analysis via spherical lens element 1360 can be correlated to interrogation results via additional fluid path interrogation interface 1370. This can provide additional analytical vectors into the properties of the fluid passing through the fluid path, particularly as it passes through analysis zone 1362. It will also be noted that the fluid path can take any form needed to provide for additional fluid path interrogation interface 1370 and is expressly not constrained to the form illustrated in system 1300, which was selected for simplicity of illustration.

Figure 14:
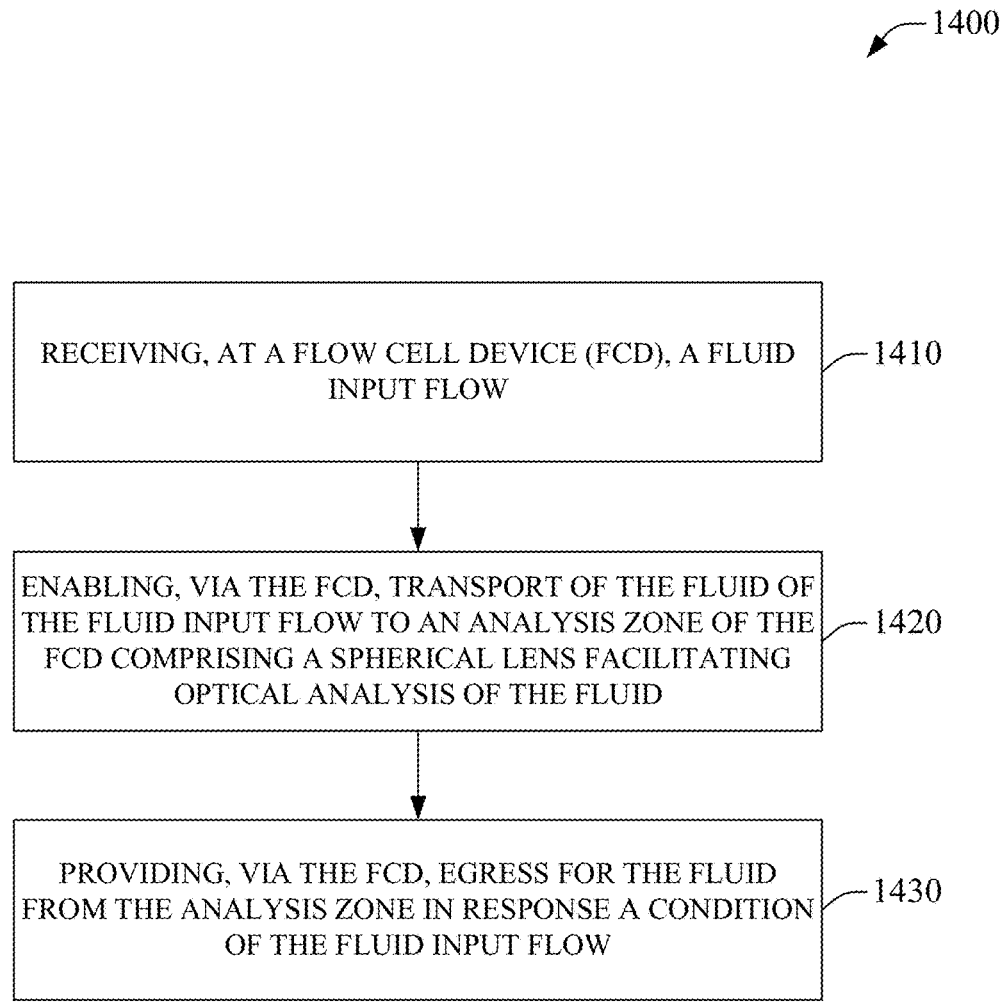
FIG. 14 illustrates an example process facilitating analysis of a fluid passing through a flow cell device including a spherical lens that enables transmitting optical energy in and out of an analysis zone of flow cell device, in accordance with aspects of the subject disclosure.
Figure 15:
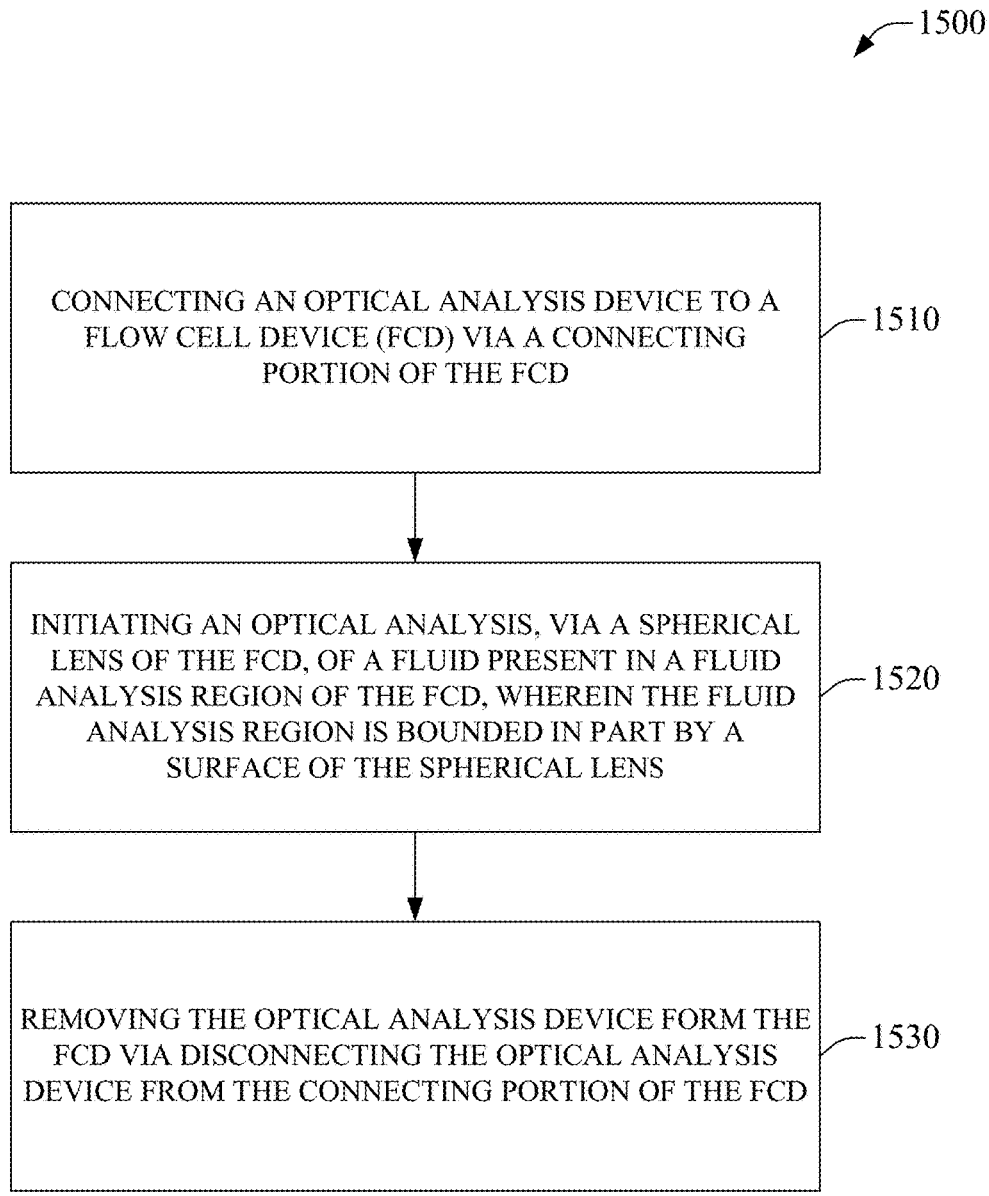
FIG. 15 illustrates an example process illustrating removably connecting an optical analysis device to a flow cell device including a spherical lens that enables transmitting optical energy in and out of an analysis zone of flow cell device, in accordance with aspects of the subject disclosure.
Figure 16:
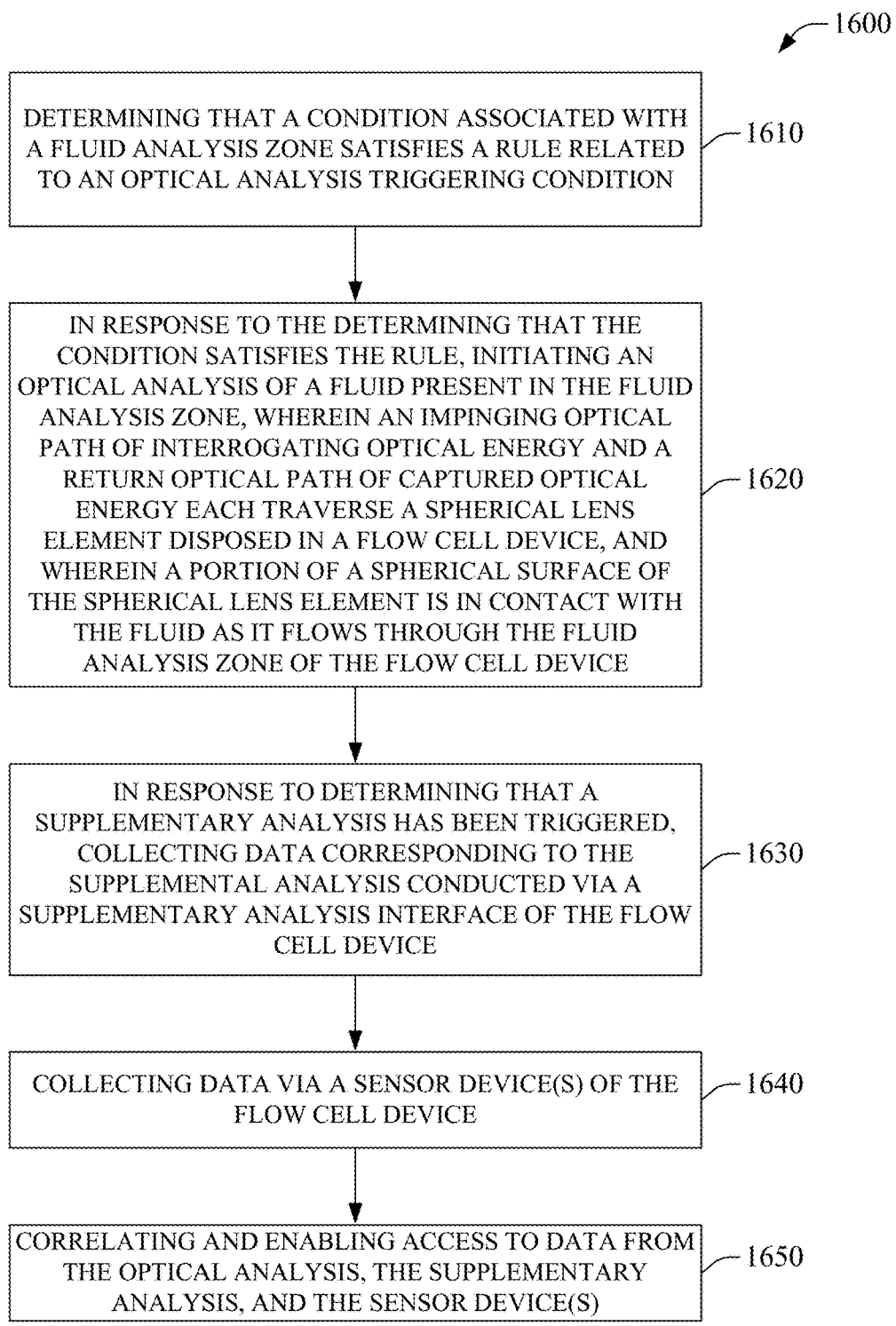
FIG. 16 illustrates an example process enabling triggering at least an optical analysis of a fluid passing through a flow cell device including a spherical lens that enables transmitting optical energy in and out of an analysis zone of flow cell device, in accordance with aspects of the subject disclosure.

In view of the example system(s) described above, example process(s) that can be implemented in accordance with the disclosed subject matter can be better appreciated with reference to flowcharts in FIG. 14-FIG. 16. For purposes of simplicity of explanation, example processes disclosed herein are presented and described as a series of acts; however, it is to be understood and appreciated that the claimed subject matter is not limited by the order of acts, as some acts may occur in different orders and/or concurrently with other acts from that shown and described herein. For example, one or more example processes disclosed herein could alternatively be represented as a series of interrelated states or events, such as in a state diagram. Moreover, interaction diagram(s) may represent processes in accordance with the disclosed subject matter when disparate entities enact disparate portions of the processes. Furthermore, not all illustrated acts may be required to implement a described example process in accordance with the subject specification. Further yet, two or more of the disclosed example processes can be implemented in combination with each other, to accomplish one or more aspects herein described. It should be further appreciated that the example processes disclosed throughout the subject specification are capable of being stored on an article of manufacture (e.g., a computer-readable medium) to allow transporting and transferring such processes to computers for execution, and thus implementation, by a processor or for storage in a memory.

FIG. 14 illustrates example process 1400 that facilitates analysis of a fluid passing through a flow cell device including a spherical lens that enables transmitting optical energy in and out of an analysis zone of flow cell device, in accordance with aspects of the subject disclosure. Process 1400, at 1410, can include, receiving, at a flow cell device (FCD), a fluid input flow. The fluid input can be received from a fluidic system, for example a petrochemical plant, pharmaceutical plant, municipal water treatment facility, etc. In an aspect, the fluidic system can include a fluid transport line that can be adapted to, or can be design to, include a FCD to facilitate optical analysis as disclosed herein.

At 1420, process 1400 can include enabling, via the FCD, transport of the fluid of the fluid input flow to an analysis zone of the FCD including a spherical lens. The spherical lens can facilitate optical analysis of the fluid in the analysis zone. The spherical lens can form a portion of a fluidic channel of the FCD.

At 1430, process 1400 can provide egress for the fluid from the analysis zone in response to a condition of the fluid input flow. At this point, process 1400 can end. In some embodiments, as additional fluid is introduced at the input of the FCD, e.g., fluid pressure is higher at the input than at the output, fluid can be pushed through the analysis zone to the fluid egress. In another embodiment, as fluid is removed from the FCD egress, e.g., fluid pressure is higher at the input than at the output, additional fluid can be introduced at the input of the FCD, resulting in fluid being pulled through the analysis zone from the input to the fluid egress.

FIG. 15 illustrates example process 1500 facilitating removably connecting an optical analysis device to a flow cell device including a spherical lens that enables transmitting optical energy in and out of an analysis zone of flow cell device, in accordance with aspects of the subject disclosure. Process 1500, at 1510, can include connecting an optical analysis device to a flow cell device (FCD) via a connecting portion of the FCD. In some embodiments, connection to the FCD can be automated. In other embodiments, the connection can be manual. In an aspect, connecting the optical analysis device to the FCD can enable the optical analysis device to initiate an optical analysis, e.g., the connection can overcome an interlock element that would otherwise prevent the optical analysis device from, for example, firing an interrogating laser without being properly connected to the FCD.

At 1520, process 1500 can include initiating an optical analysis of a fluid present in a fluid analysis region of the FCD. The optical analysis can be performed via a spherical lens of the FCD. The spherical lens can be disposed in a wall of a fluid path of the FCD as disclosed elsewhere herein. The fluid analysis region can be bounded by at least a portion of the surface of the spherical lens. As such, optical energy input into a first side of the spherical optical lens can be introduced into the fluid analysis region via a second side of the spherical optical lens to enable analysis of the fluid in situ without exposing the fluid to the external environment and without inserting the outside environment into the in situ environment.

At 1530, process 1500 can include removing the optical analysis device from the FCD. At this point process 1500 can end. Disconnecting the optical analysis device from the connecting portion of the FCD can be an automated or manual process. In some embodiments, the disconnection can reestablish aforementioned interlock condition. Moreover, in some embodiments, the disconnected optical analysis device can be moved to a different FCD, enabling additional analyses to be performed at other test points of a fluidic system.

FIG. 16 illustrates example process 1600 facilitating triggering at least an optical analysis of a fluid passing through a flow cell device including a spherical lens that enables transmitting optical energy in and out of an analysis zone of flow cell device, in accordance with aspects of the subject disclosure. Process 1600, at 1610, can include determining, by a device including a processor, that a condition associated with a fluid analysis zone satisfies a rule related to an optical analysis triggering condition. In an aspect, the condition associated with the fluid analysis zone can be determined based on data obtained regarding the fluid flowing through a flow cell device (FCD), for example, as captured by sensor device(s) 380, etc.

At 1620, process 1600 can include initiating an optical analysis in response to the determining the condition at 1610. The analysis can be of a fluid present in a fluid analysis zone. An impinging optical path of optical energy and a return path for returned optical energy can traverse a spherical lens. The spherical lens can be disposed in the flow cell device and be in contact with the fluid as it flows there through. In an aspect, where the optical analysis trigger condition is determined to occur at 1610, the optical analysis can be initiated by the processor at 1620. The optical analysis occurs via a spherical optical lens allowing external interrogation of the in situ environment of the fluid flow path through the FCD.

At 1630 of process 1600, a supplementary analysis can be performed via a supplementary analysis interface in response to determining that the supplementary analysis has been triggered. Triggering the supplementary analysis can be based on the data collected at 1610, the initiation of the optical analysis at 1620, etc. The supplementary analysis can occur, for example, via additional fluid path interrogation interface 370, 1370, etc., via sensor device(s) 380, etc., or other analytical modalities.

At 1640 of process 1600, data can be collected by the processor via a sensor device, e.g., sensor device(s) 380, etc., of the FCD. The data collection at 1640 can be in response to the optical analysis of 1620, the supplementary analysis of 1630, the triggering of 1610, etc. Sensor data can be correlated to a fluid condition, a FCD condition, an optical energy condition, a spherical optical element condition, etc. As an example, a temperature of the FCD can be monitored by a temperature sensor to evaluate a condensing condition of a gas flow through the FCD, e.g., the fluid can be a liquid, gas, slurry, suspension, heterogeneous mixture of liquid and solid, powder, aerosol or other flowing solid material (e.g., peanut butter), or any other fluid.

At 1650, process 1600 can include correlating, by the processor, data from the optical analysis, the supplementary analysis, and the sensor data. At this point process 1600 can end. Further, at 1650, access to the correlated data can be enabled by the processor. In an aspect, data access can be based on numerous criteria, such as, bandwidth, alert condition(s), available memory, etc. As an example, the correlated data can be accessed by a laboratory information management system (LIMS) component for analysis performed via FCDs located in-plant or, subject to available connectivity, out-of-plant. As another example, data can be categorized and/or ranked, to allow preservation of more critical data on a portable optical analysis device that has limited memory capacity. Similarly, for example, some data from the FCD, e.g., some, none, or all of the sensor device(s) data; some, none, or all of the supplementary analysis data, etc., may not be coordinated or stored based on a device state, e.g., a limited memory can result in storage of all or less than all of the available data for the one or more analytical modes provided by the disclosed FCD with spherical lens element. It will be noted that processing can occur, at least in part, on a processor that is located proximate to the FCD, remote from the FCD and connected via a wired and/or wireless network, on a distributed computing platform, e.g., a cloud platform, etc., as a virtualized data processing component, etc.

In some embodiments, the flow cell device (FCD) (e.g., FCD 212-1312) can be consumable or exchangeable. This can be in lieu of, or in addition to, the FCD being cleanable. It will be appreciated that repeated use of a FCD without cleaning can result in changes to the condition of the FCD that can alter captured results. As an example, flow of a viscous sample through the FCD can result in the sample adhering to an optical element of the FCD and preventing accurate results in following analytical runs of the instrument. In these situations, the FCD can be cleaned or exchanged. In an aspect, some types of samples can be affiliated with particular types of FCDs, for example, sampling of concentrated hydrofluoric acid can be better performed with a plastic lens in the FCD than a glass lens in the FCD. As another example, a first depth of focus can be desired for a first analysis and a different second depth of focus can be desired for another analysis. The disclosed subject matter can include a cleaning component to enable cleaning of a FCD. Moreover, the disclosed subject matter can include a plurality of other FCDs to allow for replacement of consumed FCDs, exchange of FCDs suited to an analysis, etc. As an example, a FCD that was used with a viscous sample can be moved to the cleaning component and a different FCD can be substituted. This can allow the analysis to continue while the first FCD is being cleaned. In another example, a damaged FCD can be disposed of and a replacement FCD can be retrieved from the repository of FCDs. In a further example, a first FCD can be used for a first analysis and then a second FCD can be used for a second analysis. Moreover, the system can, in some embodiments, check the condition of a FCD to determine if replacement of the FCD should occur, e.g., a self-diagnostic, calibration, etc.

Accordingly, in some embodiments, FCD can include, or be, a consumable component. In an aspect, a consumable FCD can include the optical element to direct optical energy at the sample. As an example, a consumable FCD can be a disposable FCD with a spherical optical element that is included in the FCD. As such, when a consumable FCD becomes dirty, damaged, ill-suited to the determined optical analysis, etc., the consumable FCD can be discarded and a replacement consumable FCD can be implemented to proceed with further analysis. A disposable FCD can be used repeatedly, and there may be situations in which replacement of the disposable FCD is desirable, e.g., to prevent cross contamination, damage to the FCD, fouling of the FCD, etc. Similarly, a consumable FCD can allow continued use of an optical element until it is determined that the consumable FCD should be replaced with another consumable FCD. In an aspect, the replacement consumable FCD can be the same, similar to, or different from, the consumable FCD being replaced.

Moreover, in some embodiments, a consumable FCD can be constructed of nearly any material. A consumable FCD can include a suitable polymer. A consumable FCD can include other materials, such as, but not limited to, stainless steel, gold, or other metal; borosilicate or other glass; starches or other carbohydrates, etc.; or nearly any other material suitable to a particular sample environment. Moreover, materials can be machined, sintered, cast, injection molded, 3D-printed, etc., for example to form a body, etc., of the consumable FCD. In an example, the consumable FCD can include an optical element that can be generally spherical. The optical element can be separately manufactured and added to the body of a consumable FCD, either as part of a molding process, bonded with an adhesive, attached with a friction or press fit, mechanically captured, etc. In other embodiments, the spherical optical element can be co-formed with the body as part of a molding process, e.g., the spherical optical element can be formed, of the same or a different material, as the consumable FCD body, such as by injection molding; can be formed, of the same or a different material, as the consumable FCD via 3D printing; etc. Additionally, spherical optical elements can be manufactured from nearly any appropriate material, including the same or different materials as the body of the consumable FCD. Non-limiting examples of appropriate materials can include a polymer, sapphire, glass, mineral, etc., depending on the optical properties suited to a given scenario.

Figure 17:
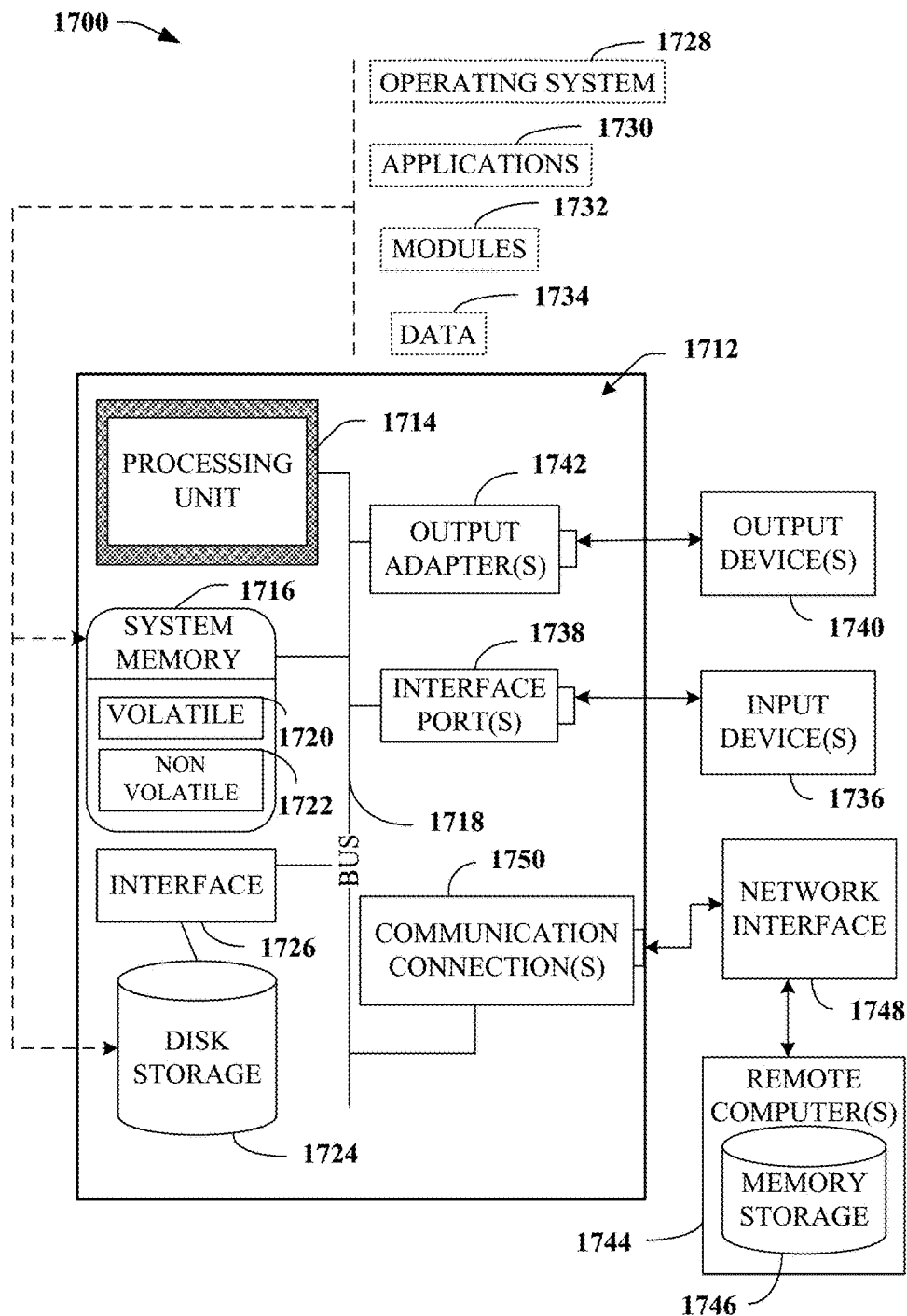
FIG. 17 illustrates an example block diagram of a computing system operable to execute the disclosed systems and processes in accordance with some embodiments.

FIG. 17 illustrates a block diagram of a computing system 1700 operable to execute the disclosed systems and processes in accordance with some embodiments. Computer 1712, which can be, for example, included in optical analysis component 150, fluidic system component 102, FCD 212-1312, sensor device(s) 380, etc., can include a processing unit 1714, a system memory 1716, and a system bus 1718. System bus 1718 couples system components including, but not limited to, system memory 1716 to processing unit 1714. Processing unit 1714 can be any of various available processors. Dual microprocessors and other multiprocessor architectures also can be employed as processing unit 1714.

System bus 1718 can be any of several types of bus structure(s) including a memory bus or a memory controller, a peripheral bus or an external bus, and/or a local bus using any variety of available bus architectures including, but not limited to, industrial standard architecture, micro-channel architecture, extended industrial standard architecture, intelligent drive electronics, video electronics standards association local bus, peripheral component interconnect, card bus, universal serial bus, advanced graphics port, personal computer memory card international association bus, Firewire (Institute of Electrical and Electronics Engineers 1194), and small computer systems interface.

System memory 1716 can include volatile memory 1720 and nonvolatile memory 1722. A basic input/output system, containing routines to transfer information between elements within computer 1712, such as during start-up, can be stored in nonvolatile memory 1722. By way of illustration, and not limitation, nonvolatile memory 1722 can include read only memory, programmable read only memory, electrically programmable read only memory, electrically erasable read only memory, or flash memory. Volatile memory 1720 includes read only memory, which acts as external cache memory. By way of illustration and not limitation, read only memory is available in many forms such as synchronous random access memory, dynamic read only memory, synchronous dynamic read only memory, double data rate synchronous dynamic read only memory, enhanced synchronous dynamic read only memory, SynchLink dynamic read only memory, Rambus direct read only memory, direct Rambus dynamic read only memory, and Rambus dynamic read only memory.

Computer 1712 can also include removable/non-removable, volatile/non-volatile computer storage media. FIG. 17 illustrates, for example, disk storage 1724. Disk storage 1724 includes, but is not limited to, devices like a magnetic disk drive, floppy disk drive, tape drive, flash memory card, or memory stick. In addition, disk storage 1724 can include storage media separately or in combination with other storage media including, but not limited to, an optical disk drive such as a compact disk read only memory device, compact disk recordable drive, compact disk rewritable drive or a digital versatile disk read only memory. To facilitate connection of the disk storage devices 1724 to system bus 1718, a removable or non-removable interface is typically used, such as interface 1726.

Computing devices typically include a variety of media, which can include computer-readable storage media or communications media, which two terms are used herein differently from one another as follows.

Computer-readable storage media can be any available storage media that can be accessed by the computer and includes both volatile and nonvolatile media, removable and non-removable media. By way of example, and not limitation, computer-readable storage media can be implemented in connection with any process or technology for storage of information such as computer-readable instructions, program modules, structured data, or unstructured data. Computer-readable storage media can include, but are not limited to, read only memory, programmable read only memory, electrically programmable read only memory, electrically erasable read only memory, flash memory or other memory technology, compact disk read only memory, digital versatile disk or other optical disk storage, magnetic cassettes, magnetic tape, magnetic disk storage or other magnetic storage devices, or other tangible media which can be used to store desired information. In this regard, the term "tangible" herein as may be applied to storage, memory or computer-readable media, is to be understood to exclude only propagating intangible signals per se as a modifier and does not relinquish coverage of all standard storage, memory or computer-readable media that are not only propagating intangible signals per se. In an aspect, tangible media can include non-transitory media wherein the term "non-transitory" herein as may be applied to storage, memory or computer-readable media, is to be understood to exclude only propagating transitory signals per se as a modifier and does not relinquish coverage of all standard storage, memory or computer-readable media that are not only propagating transitory signals per se. Computer-readable storage media can be accessed by one or more local or remote computing devices, e.g., via access requests, queries or other data retrieval protocols, for a variety of operations with respect to the information stored by the medium. As such, for example, a computer-readable medium can include executable instructions stored thereon that, in response to execution, can cause a system including a processor to perform operations, including determining satisfaction of triggering conditions, conditions relating to a property of a fluid in a analysis zone, sensor device(s) data, etc.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

It can be noted that FIG. 17 describes software that acts as an intermediary between users and computer resources described in suitable operating environment 1700. Such software includes an operating system 1728. Operating system 1728, which can be stored on disk storage 1724, acts to control and allocate resources of computer system 1712. System applications 1730 take advantage of the management of resources by operating system 1728 through program modules 1732 and program data 1034 stored either in system memory 1716 or on disk storage 1724. It is to be noted that the disclosed subject matter can be implemented with various operating systems or combinations of operating systems.

A user can enter commands or information into computer 1712 through input device(s) 1736. In some embodiments, a user interface can allow entry of user preference information, etc., and can be embodied in a touch sensitive display panel, a mouse/pointer input to a graphical user interface (GUI), a command line controlled interface, etc., allowing a user to interact with computer 1712. Input devices 1736 include, but are not limited to, a pointing device such as a mouse, trackball, stylus, touch pad, keyboard, microphone, joystick, game pad, satellite dish, scanner, TV tuner card, digital camera, digital video camera, web camera, cell phone, smartphone, tablet computer, etc. These and other input devices connect to processing unit 1714 through system bus 1718 by way of interface port(s) 1738. Interface port(s) 1738 include, for example, a serial port, a parallel port, a game port, a universal serial bus, an infrared port, a Bluetooth port, an IP port, or a logical port associated with a wireless service, etc. Output device(s) 1740 use some of the same type of ports as input device(s) 1736.

Thus, for example, a universal serial busport can be used to provide input to computer 1712 and to output information from computer 1712 to an output device 1740. Output adapter 1042 is provided to illustrate that there are some output devices 1740 like monitors, speakers, and printers, among other output devices 1740, which use special adapters. Output adapters 1742 include, by way of illustration and not limitation, video and sound cards that provide means of connection between output device 1740 and system bus 1718. It should be noted that other devices and/or systems of devices provide both input and output capabilities such as remote computer(s) 1744.

Computer 1712 can operate in a networked environment using logical connections to one or more remote computers, such as remote computer(s) 1744. Remote computer(s) 1744 can be a personal computer, a server, a router, a network PC, cloud storage, a cloud service, code executing in a cloud-computing environment, a workstation, a microprocessor based appliance, a peer device, or other common network node and the like, and typically includes many or all of the elements described relative to computer 1712. A cloud computing environment, the cloud, or other similar terms can refer to computing that can share processing resources and data to one or more computer and/or other device(s) on an as needed basis to enable access to a shared pool of configurable computing resources that can be provisioned and released readily. Cloud computing and storage solutions can store and/or process data in third-party data centers which can leverage an economy of scale and can view accessing computing resources via a cloud service in a manner similar to a subscribing to an electric utility to access electrical energy, a telephone utility to access telephonic services, etc.

For purposes of brevity, only a memory storage device 1746 is illustrated with remote computer(s) 1744. Remote computer(s) 1744 is logically connected to computer 1712 through a network interface 1748 and then physically connected by way of communication connection 1750. Network interface 1748 encompasses wire and/or wireless communication networks such as local area networks and wide area networks. Local area network technologies include fiber distributed data interface, copper distributed data interface, Ethernet, Token Ring and the like. Wide area network technologies include, but are not limited to, point-to-point links, circuit-switching networks like integrated services digital networks and variations thereon, packet switching networks, and digital subscriber lines. As noted below, wireless technologies may be used in addition to or in place of the foregoing.

Communication connection(s) 1750 refer(s) to hardware/software employed to connect network interface 1748 to bus 1718. While communication connection 1750 is shown for illustrative clarity inside computer 1012, it can also be external to computer 1712. The hardware/software for connection to network interface 1748 can include, for example, internal and external technologies such as modems, including regular telephone grade modems, cable modems and digital subscriber line modems, integrated services digital network adapters, and Ethernet cards.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

As it employed in the subject specification, the term "processor" can refer to substantially any computing processing unit or device including, but not limited to including, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit, a digital signal processor, a field programmable gate array, a programmable logic controller, a complex programmable logic device, a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

As used in this application, the terms "component," "system," "platform," "layer," "selector," "interface," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. Moreover, the use of any particular embodiment or example in the present disclosure should not be treated as exclusive of any other particular embodiment or example, unless expressly indicated as such, e.g., a first embodiment that has aspect A and a second embodiment that has aspect B does not preclude a third embodiment that has aspect A and aspect B. The use of granular examples and embodiments is intended to simplify understanding of certain features, aspects, etc., of the disclosed subject matter and is not intended to limit the disclosure to said granular instances of the disclosed subject matter or to illustrate that combinations of embodiments of the disclosed subject matter were not contemplated at the time of actual or constructive reduction to practice.

As will be understood by one of ordinary skill in the art, each embodiment disclosed herein can include, consist essentially of or consist of its particular stated element, step, ingredient or component. Thus, the terms "include" or "including" should be interpreted to recite: "include, consist of, or consist essentially of." The transition term "include" or "includes" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities, machine learning components, or automated components (e.g., supported through artificial intelligence, as through a capacity to make inferences based on complex mathematical formalisms), that can provide simulated vision, sound recognition and so forth.

The term "infer" or "inference" can generally refer to the process of reasoning about, or inferring states of, the system, environment, user, and/or intent from a set of observations as captured via events and/or data. Captured data and events can include user data, device data, environment data, data from sensors, sensor data, application data, implicit data, explicit data, etc. Inference, for example, can be employed to identify a specific context or action, or can generate a probability distribution over states of interest based on a consideration of data and events. Inference can also refer to techniques employed for composing higher-level events from a set of events and/or data. Such inference results in the construction of new events or actions from a set of observed events and/or stored event data, whether the events, in some instances, can be correlated in close temporal proximity, and whether the events and data come from one or several event and data sources. Various classification schemes and/or systems (e.g., support vector machines, neural networks, expert systems, Bayesian belief networks, fuzzy logic, and data fusion engines) can be employed in connection with performing automatic and/or inferred action in connection with the disclosed subject matter.

What has been described above includes examples of systems and processes illustrative of the disclosed subject matter. It is, of course, not possible to describe every combination of components or processes herein. One of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "including" as "including" is interpreted when employed as a transitional word in a claim.

What is claimed is:

1. A system comprising:
a flow cell device having defined therein a fluid path, the flow cell device comprising:
an input connection for receiving a fluid into the fluid path; and
an output connection for egress of the fluid from the fluid path;
a spherical lens coupled to the flow cell device, defining a portion of a boundary of the fluid path, and providing optical access to an analysis region of the fluid path; and
an optical analysis device connector providing a removable connection of the system to an optical analysis device that employs the optical access to the analysis region via the spherical lens to optically interrogate at least a portion of the fluid that passes through the analysis region.

2. The system of claim 1, wherein the fluid is a gas.

3. The system of claim 1, wherein the fluid is a liquid.

4. The system of claim 1, wherein the fluid is a slurry, a suspension, or a heterogeneous mixture of liquid and solid.

5. The system of claim 1, wherein the fluid is a powder, an aerosol, or a flowing solid material.

6. The system of claim 1, wherein the spherical lens is sealed into an orifice defined in the flow cell device to provide the optical access while preventing leaking of the fluid between the spherical lens and the orifice.

7. The system of claim 6, wherein the spherical lens is sealed into the orifice by an elastomer.

8. The system of claim 6, wherein the spherical lens is sealed into the orifice by a metal that is deformable without damage to the spherical lens.

9. The system of claim 1, wherein the optical analysis device is a Raman spectrometer.

10. The system of claim 1, wherein spherical lens is a sapphire spherical lens.

11. The system of claim 1, wherein the input connection couples to a component of a fluidic system, the component of the fluidic system comprising at least one of a pressure fitting, a tapered threaded device, a parallel threaded device, a quick-connect device, a face-sealed device, a piston sealed device, a ferrule compression device, a conical device, a coned-and-threaded device, a welded device, a brazed device, or a soldered device.

12. The system of claim 1, wherein a body of the flow cell device comprises metal.

13. The system of claim 1, wherein a body of the flow cell device comprises a polymer.

14. The system of claim 1, wherein a body of the flow cell device comprises ceramic material.

15. The system of claim 1, wherein a body of the flow cell device is of a different material than a component of the flow cell device that defines a remaining portion of the boundary of the fluid path.

16. A method comprising:
receiving, at a flow cell device, a fluid;
transporting the fluid to an analysis zone of the flow cell device, wherein the analysis zone is bounded by at least a portion of a surface of a spherical lens that facilitates optical interrogation of the fluid in the analysis zone; and
enabling egress for the fluid from the flow cell device after the fluid passes the analysis zone.

17. The method of claim 16, wherein the transporting comprises transporting a liquid fluid or a gas fluid.

18. The method of claim 16, wherein the transporting the fluid comprises transporting the fluid against a seal between the spherical lens and a portion of the flow cell device defining a boundary of the analysis zone, and wherein the seal is enabled by at least one of an elastomer, a polymer, an epoxy, or a deformable metal.

19. The method of claim 16, wherein the optical interrogation is enabled by a Raman spectrometer removably connected to the flow cell device via an optical analysis device connector.

20. The method of claim 16, further comprising:
triggering, by the flow cell device, the optical interrogation of the fluid in the analysis zone based on a condition of the fluid in the analysis zone being determined to satisfy a trigger rule, wherein the condition is based on data collected by a sensor device of the flow cell device.

21. A system comprising:
a flow cell device having defined therein a fluid path to receive a fluid into the fluid path and to allow the fluid to egress from the fluid path;
a spherical lens sealed into an orifice defined in the flow cell device at a portion of a boundary of the fluid path, the spherical lens to provide optical access to an analysis region of the fluid path while preventing leaking of the fluid between the spherical lens and the orifice; and
an optical analysis device connector providing a connection of the system to an optical analysis device that employs the optical access to the analysis region via the spherical lens to optically interrogate at least a portion of the fluid that passes through the analysis region.

22. The system of claim 21, wherein the spherical lens is sealed into the orifice by at least one of an elastomer, a polymer, or a metal that is deformable.

* * * * *